United States Patent
Genkin et al.

(10) Patent No.: US 11,701,410 B2
(45) Date of Patent: Jul. 18, 2023

(54) EXTRACELLULAR DNA AS A THERAPEUTIC TARGET IN NEURODEGENERATION

(71) Applicant: CLS THERAPEUTICS LIMITED, Saint Peter Port (GG)

(72) Inventors: Dmitry Dmitrievich Genkin, Saint Petersburg (RU); Georgy Viktorovich Tets, Saint Petersburg (RU); Viktor Veniaminovich Tets, Saint Petersburg (RU)

(73) Assignee: CLS THERAPEUTICS LIMITED, Saint Peter Port (GG)

( * ) Notice: Subject to any disclaimer, the term of this patent is extended or adjusted under 35 U.S.C. 154(b) by 0 days.

(21) Appl. No.: 15/576,611

(22) PCT Filed: May 11, 2016

(86) PCT No.: PCT/RU2016/000284
§ 371 (c)(1),
(2) Date: Nov. 22, 2017

(87) PCT Pub. No.: WO2016/190780
PCT Pub. Date: Dec. 1, 2016

(65) Prior Publication Data
US 2018/0360925 A1 Dec. 20, 2018

Related U.S. Application Data

(60) Provisional application No. 62/165,255, filed on May 22, 2015.

(51) Int. Cl.
| | |
|---|---|
| *A61K 38/46* | (2006.01) |
| *A61K 47/61* | (2017.01) |
| *A61K 9/00* | (2006.01) |
| *A61P 25/28* | (2006.01) |
| *A61P 25/18* | (2006.01) |
| *A61P 25/16* | (2006.01) |

(52) U.S. Cl.
CPC .......... *A61K 38/465* (2013.01); *A61K 9/0019* (2013.01); *A61K 9/0053* (2013.01); *A61K 9/0085* (2013.01); *A61K 47/61* (2017.08); *A61P 25/16* (2018.01); *A61P 25/18* (2018.01); *A61P 25/28* (2018.01); *C12Y 301/02021* (2013.01); *C12Y 301/21001* (2013.01)

(58) Field of Classification Search
None
See application file for complete search history.

(56) References Cited

U.S. PATENT DOCUMENTS

| | | |
|---|---|---|
| 3,224,942 A | 12/1965 | Martin |
| 4,485,095 A | 11/1984 | Fujisaki et al. |
| 5,484,589 A | 1/1996 | Salganik |
| 5,656,589 A | 8/1997 | Stossel et al. |
| 5,830,744 A | 11/1998 | Rosen et al. |
| 5,855,920 A | 1/1999 | Chein |
| 5,889,153 A | 3/1999 | Suzuki et al. |
| 5,952,170 A | 9/1999 | Stroun et al. |
| 6,033,846 A | 3/2000 | Fournie |
| 6,156,504 A | 12/2000 | Gocke et al. |
| 6,391,607 B1 | 5/2002 | Lazarus et al. |
| 6,428,785 B1 | 8/2002 | Gokcen |
| 6,455,250 B1 | 9/2002 | Aguilera et al. |
| 6,465,177 B1 | 10/2002 | Hoon |
| 6,521,409 B1 | 2/2003 | Gocke et al. |
| 7,297,526 B2 | 11/2007 | Shak |
| 7,402,724 B2 | 7/2008 | Conover |
| 7,612,032 B2 | 11/2009 | Genkin et al. |
| 8,388,951 B2 | 3/2013 | Genkin et al. |
| 8,431,123 B2* | 4/2013 | Genkin .................. A61K 38/46 424/94.6 |
| 8,535,663 B2 | 9/2013 | Genkin et al. |
| 8,710,012 B2 | 4/2014 | Genkin et al. |
| 8,759,004 B2 | 6/2014 | Coy |
| 8,796,004 B2 | 8/2014 | Genkin et al. |
| 8,871,200 B2 | 10/2014 | Genkin et al. |
| 9,695,220 B2 | 4/2017 | Vandenberghe et al. |
| 2003/0044403 A1 | 3/2003 | Shak |
| 2004/0001817 A1 | 1/2004 | Giampapa |
| 2004/0157239 A1 | 8/2004 | Tanuma et al. |
| 2006/0228347 A1 | 10/2006 | Sunaga et al. |
| 2006/0233780 A1 | 10/2006 | Genkin et al. |
| 2007/0104702 A1 | 5/2007 | Genkin et al. |

(Continued)

FOREIGN PATENT DOCUMENTS

| | | |
|---|---|---|
| CA | 2184582 A1 | 9/1995 |
| CA | 2394856 A1 | 6/2001 |

(Continued)

OTHER PUBLICATIONS

Glebova, K.V. et al. 2014. Properties of extracellular DNA from the cerebrospinal fluid and blood plasma during Parkinson's disease. Bulletin of Experimental Biology and Medicine 156(6): 826-828. specif. pp. 826, 827.*

Trysberg, E. et al. 2004. Cerebral inflammation and degeneration in systemic lupus erythematosus. Current Opinion in Rheumatology 16: 527-533. specif. pp. 527, 529.*

Nicolson, G.L. 2008. Chronic bacterial and viral infecrtions in neurodegenerative and neurobehavioral diseases. Lab Medicine 39(5):291-299. specif.pp. 291, 294.*

Morell, A.G. et al. 1971. The role of sialic acid in determining the survival of glycoproteins in the circulation. Journal of Biological Chemistry 246(5): 1461-1467. specif. pp. 1461, 1464.*

(Continued)

*Primary Examiner* — Renee Claytor
*Assistant Examiner* — Sharon M. Papciak
(74) *Attorney, Agent, or Firm* — Entralta PLLC; James F. Fleming; Peter D. Weinstein

(57) ABSTRACT

The invention relates to the use of deoxyribonuclease (DNase) enzyme for inhibiting progression and for prevention and treatment of neurodegeneration.

30 Claims, 3 Drawing Sheets
Specification includes a Sequence Listing.

(56) References Cited

U.S. PATENT DOCUMENTS

| | | |
|---|---|---|
| 2008/0004561 A1 | 1/2008 | Genkin et al. |
| 2009/0047272 A1 | 2/2009 | Appelbaum et al. |
| 2009/0053200 A1 | 2/2009 | Genkin et al. |
| 2010/0061971 A1 | 3/2010 | Genkin et al. |
| 2010/0150903 A1 | 6/2010 | Genkin et al. |
| 2010/0303796 A1* | 12/2010 | Genkin ............... A61K 38/465 424/94.6 |
| 2011/0033438 A1 | 2/2011 | Bartoov et al. |
| 2011/0070201 A1 | 3/2011 | Shaaltiel et al. |
| 2011/0189156 A1 | 8/2011 | Genkin et al. |
| 2012/0252750 A1 | 4/2012 | Shea et al. |
| 2013/0183283 A1 | 7/2013 | Genkin et al. |
| 2013/0183284 A1 | 7/2013 | Genkin et al. |
| 2013/0209443 A9 | 8/2013 | Genkin et al. |
| 2013/0216516 A1 | 8/2013 | Genkin et al. |
| 2014/0193389 A1 | 7/2014 | Genkin et al. |
| 2015/0010523 A1 | 1/2015 | Genkin et al. |
| 2015/0010527 A1 | 1/2015 | Shaaltiel et al. |
| 2015/0110769 A1 | 4/2015 | Genkin et al. |
| 2016/0130570 A1 | 5/2016 | Genkin et al. |
| 2016/0303204 A1 | 10/2016 | Genkin et al. |
| 2017/0216456 A1 | 8/2017 | Alexander et al. |

FOREIGN PATENT DOCUMENTS

| | | | |
|---|---|---|---|
| DE | 4024530 A1 | | 2/1992 |
| DE | 10221194 A1 | | 12/2003 |
| EP | 0325191 A2 | | 7/1989 |
| EP | 1431762 A1 | | 6/2004 |
| EP | 1655036 A1 | | 5/2006 |
| EP | 1661579 A2 | | 5/2006 |
| EP | 1666055 A1 | | 6/2006 |
| EP | 1880733 A1 | | 1/2008 |
| EP | 2095825 A1 | | 9/2009 |
| EP | 2497488 A1 | | 9/2012 |
| GB | 984464 A | | 2/1965 |
| GB | 1005985 A | | 9/1965 |
| IL | 199005 B | * | 4/2012 |
| JP | 61293927 A | | 12/1986 |
| JP | 2000-229881 A | | 8/2000 |
| JP | 2006290769 A | | 10/2006 |
| JP | 2010-511039 A | | 4/2010 |
| NZ | 299257 A | | 7/2000 |
| RU | 2099080 C1 | | 12/1997 |
| RU | 2202109 C1 | | 4/2003 |
| RU | 2207876 C1 | | 7/2003 |
| RU | 2227029 C2 | | 4/2004 |
| RU | 2239404 C1 | | 11/2004 |
| RU | 2239442 C1 | | 11/2004 |
| RU | 2267329 C2 | | 1/2006 |
| RU | 2269357 C2 | | 2/2006 |
| RU | 2269359 C2 | | 2/2006 |
| RU | 2308968 C2 | | 10/2007 |
| WO | 1993/03709 A1 | | 3/1993 |
| WO | 1995/00170 A1 | | 1/1995 |
| WO | 1997/28266 A1 | | 8/1997 |
| WO | 1997/47751 A1 | | 12/1997 |
| WO | 199904632 A1 | | 2/1999 |
| WO | 2000/003709 A1 | | 1/2000 |
| WO | 2000/031238 A2 | | 6/2000 |
| WO | 2001/074905 A1 | | 10/2001 |
| WO | 2001/82949 A1 | | 11/2001 |
| WO | 2003/068254 A1 | | 8/2003 |
| WO | 2005004789 A2 | | 1/2005 |
| WO | 2005004903 A1 | | 1/2005 |
| WO | 2005004904 A1 | | 1/2005 |
| WO | 2005007187 A1 | | 1/2005 |
| WO | 2005/115444 A2 | | 12/2005 |
| WO | 2006/130034 A1 | | 12/2006 |
| WO | 2008/039989 A2 | | 4/2008 |
| WO | 2008047364 A2 | | 4/2008 |
| WO | 2008/066403 A1 | | 6/2008 |
| WO | 2011/073665 A1 | | 6/2011 |
| WO | 2012/075506 A2 | | 6/2012 |
| WO | 2013123503 A1 | | 8/2013 |
| WO | 2014/020564 A1 | | 2/2014 |
| WO | 2015054653 A2 | | 4/2015 |
| WO | 2016081811 A1 | | 5/2016 |
| WO | 2016190780 A1 | | 12/2016 |
| WO | 2017077451 A1 | | 5/2017 |
| WO | 2017/147446 A1 | | 8/2017 |

OTHER PUBLICATIONS

Eun, H.-M. Nucleases. In: Enzymology Primer for Recombinant DNA Technology. Copyright 1996 Elsevier Inc.; a division of Academic Press. pp. 145-159. specif. p. 156.*

Podolski, J.L. et al. 1988. Association of deoxyribonuclease I with the pointed ends of actin filaments in human red blood cell membrane skeletons. Journal of Biological Chemistry 263(2): 638-645. specif. pp. 638, 643.*

Zhang, J. et al. 1999. Parkinson's disease is associated with oxidative damage to cytoplasmic DNA and RNA in substantia nigra neurons. American Journal of Pathology 154(5): 1423-1429. specif. pp. 1423, 1424.*

Klein, C. et al. 2012. Genetics of Parkinson's disease. Cold Spring Harbor Perspectives in Medicine 2: 1-15. specif. p. 1.*

Migliore, L. et al. 2001. Chromosome and oxidative damage biomarkers in lymphocytes of Parkinson's disease in patients. International Journal of Hygiene and Environmental Health 204: 61-66. specif. p. 61.*

Migliore, L. et al. 2005. Oxidative DNA damage in peripheral leukocytes of mild cognitive impairment and AD patients. Neurobiology of Aging 26: 567-573. specif. pp. 567, 568, 571.*

Cooke, M.S. et al. 2003. Oxidative DNA damage: mechanisms, mutation, and disease. FASEB Journal 17: 1195-1214. specif. pp. 1204, 1208.*

Glebova, K.V. et al. Apr. 2014. Translated from a 2013 publication. Properties of extracellular DNA from the cerebrospinal fluid and blood plasma during Parkinson's disease. Bulletin of Experimental Biology and Medicine 156(6): 826-828. specif. pp. 826, 827, 828.*

Gehrke, N. et al. 2013. Oxidative damage of DNA confers resistance to cytosolic nuclease TREX1 degradation and potentiates STING-Dependent immune sensing. Immunity 39: 482-495. specif. p. 487, Fig. S5.*

Yamaguchi, H. et al. 2006. MTH1, an oxidized purine nucleoside triphosphate, protects dopamine neurons from oxidative damage in nucleic acids caused by 1-methyl-4-phenyl-1,2,3,6-tetrahydropyridine. Cell Death and Differentiation 13: 551-563. specif. p. 552.*

Emilien, G., et al., "Pharmacological Management of Diabetes: Recent Progress and Future Perspective in Daily Drug Treatment," Pharmacology & Therapeutics, 1999, vol. 81, No. 1, pp. 37-51.

Epstein, S.E., et al., "Infection and Atherosclerosis: Potential Roles of Pathogen Burden and Molecular Mimicry," Arterioscler Thrombosis Vascular Biology, 2000, vol. 20, No. 6, pp. 1417-1420.

Erickson, R.P., "Somatic Gene Mutation and Human Disease Other than Cancer," Mutation Research, 2003, vol. 543, Issue 2, pp. 125-136.

Erickson, R.P., "Somatic Gene Mutation and Human Disease Other than Cancer: An Update," Mutation Research, 2010, vol. 705, Issue 2, pp. 96-106.

Favorov, P.V., "Issledovanie kinetiki prevrashcheny DNK pod deystviem DNK-topoizomeraz I DNK-abzimov, author's abstract of PhD thesis in biological sciences, M.," 1999, pp. 3-4, (Reference in Russian and English-language translation).

Finlay, B.J., "The Global Diversity Protozoa and Other Small Species," International Journal of Parasitology, 1998, vol. 28, Issue 1, pp. 29-48.

Freshney, R. I., "Culture of Animal Cells: A Manual of Basic Technique," Alan R. Liss, Inc., 1983, pp. 3-4.

Funakoshi, A., et al., "Clinical Investigation of Serum Deoxyribonuclease: II. Clinical Studies of Serum Deoxyribonuclease Activity in Pancreatic Disease," Gastroenterologia Japonica, 1979, vol. 14, Issue 5, pp. 436-440.

Gal, S., et al., "Detection and Quantification of Circulating Plasmodium Falciparum DNA by Polymerase Chain Reaction," Methods in Molecular Biology, 2006, vol. 336, pp. 155-162.

(56) References Cited

OTHER PUBLICATIONS

Gannushkina, I.V., et al., "Plasma DNA Levels in Patients with Atherosclerotic Involvement of the Major Arteries of the Head and lateral Amyotrophic Sclerosis, Bulletin of Experimental Biology and Medicine," 1997, vol. 124, Issue 6, pp. 1164-1166 (Translated from: Gannushkina LV. et al., 'Uroven DNK v plazme krovi bolnykh s arterosklerotichekim porazheniem magistralnykh artery golovy I bokovym amiotroficheskim sklerozom, Byulleten' Experimental'noi Biologii i Meditsiny, Moscow, Meditsina, No. 12, pp. 610-612, 1997).

Gibbs, J.B., "Mechanism-Based Target Identification and Drug Discovery in Cancer Research Science," Science, 2000, vol. 287, pp. 1969-1973.

Gibson, R.L., "Pathophysiology and Management of Pulmonary Infections in Cystic Fibrosis," American Journal of Respiratory and Critical Care Medicine, 2003, vol. 168, No. 8, pp. 918-951.

Glebova, K.V., et al., "Properties of Extracellular DNA from the Cerebrospinal Fluid and Blood Plasma during Parkinson's Disease," Bulletin of Experimental Biology and Medicine, 2014, vol. 156, Issue 6, pp. 826-828.

Gluhov, B.M., "Znachenije nukleaz v patogeneze neirovirusnyh zabolevanij, Avtoreferat dissertatsii na soiskanie uchenoi stepeni doktora medicinskikh nauk (author's abstract of MD thesis in medical sciences)," Novosibirsk, pp. 15-16, 21-26, 1996 (Reference in Russian and English-language translation of pp. 14-17 and 20-27).

Gormally, E., et al., "Circulating Free DNA in Plasma or Serum as Biomarker of Carcinogenesis: Practical Aspects and Biological Significance," Mutation Research, 2007, vol. 635, Issues 2-3, pp. 105-117.

Gorrini, C., et al., "Effect of Apoptogenic Stimuli on Colon Carcinoma Cell Lines with a Different c-myc Expression Level," International Journal of Molecular Medicine, 2003, vol. 11, No. 6, pp. 737-742.

Gould, K.L., "New Concepts and Paradigms in Cardiovascular Medicine: The Noninvasive Management of Coronary Artery Disease," The American Journal of Medicine, 1998, vol. 104, pp. 2s-17s.

Graham, R.M., "Cyclosporine: Mechanisms of Action and Toxicity," Cleaveland Clinic Journal of Medicine, 1994, vol. 61, No. 4, pp. 308-313.

Gura, T., "Systems for Identifying New Drugs Are Often Faulty," Science, 1997, vol. 278, pp. 1041-1042.

Hakkim, A., et al., "Impairment of Neutrophil Extracellular Trap Degradation is Associated with Lupus Nephritis," PNAS, 2010, vol. 107, No. 21, pp. 9813-9818.

Hann, B., et al., "Building 'Validated' Mouse Models of Human Cancer," Current Opinion in Cell Biology, 2001, vol. 13, Issue 6, pp. 778-784.

Harley, C., "Telomere Loss: Miotic Clock or Genetic Time Bomb?," Mutation Resrarch/DNAging, 1991, vol. 256, Issue 2-6, pp. 271-281.

Hawes, M.C., et al., "Extracellular DNA: A Bridge to Cancer," Cancer Research, 2015, vol. 75, No. 20, pp. 4260-4264.

Hayflick, L., "Aging Under Glass," Department of Medical Microbiology, Stanford University School of Medicine, 1970, pp. 291-303.

Hayflick, L., "The Limited in Vitro Lifetime of Human Diploid Cell Stains," Experimental Cell Research, 1965, vol. 37, pp. 614-635.

Hayflick, L., et al., "The Serial Cultivation of Human Diploid Cell Stains," Experimental Cell Research, 1961, vol. 25, pp. 585-621.

Holterhus, P-M., et al., "Mosaicism Due to a Somatic Mutation of the Androgen Receptor Gene Determines Phenotype in Androgen Insensitivity Syndrome," Journal of Clinical Endocrinology & Metabolism, 1997, vol. 82, Issue 11, pp. 3584-3589.

Horlitz, M., et al., "Optimized Quantification of Fragmented, Free Circulating DNA in Human Blood Plasma Using a Calibrated Duplex Real-Time PCR," PLoS ONE, 2009, vol. 4, Issue 9, e7207, total 6 pages.

Hursting, S.D., et al., "Calorie Restriction, Aging and Cancer Prevention: Mechanisms of Action and Applicability to Humans," Annual Review of Medicine, 2003, vol. 54, pp. 131-152.

Huttunen, R., et al., "Fatal Outcome in Bacteremia is Characterized by High Plasma Cell Free DNA Concentration and Apoptotoc DNA Fragmentation: A Prospective Cohort Study," PLoS ONE, 2011, vol. 6, e21700, total 8 pages.

International Search Report and Written Opinion for PCT/RU2015/000721, dated Aug. 25, 2016.

International Search Report and Written Opinion for PCT/RU2016/000284, dated Nov. 10, 2016.

International Search Report for PCT/GB2011/051557, dated Feb. 27, 2012.

International Search Report for PCT/RU2003/000304, dated Mar. 25, 2004.

International Search Report for PCT/RU2004/000260, dated Dec. 9, 2004.

International Search Report for PCT/RU2004/000261, dated Oct. 21, 2004.

International Search Report for PCT/RU2004/000262, dated Oct. 21, 2004.

International Search Report for PCT/RU2005/000236, dated Nov. 24, 2005.

International Search Report for PCT/RU2006/000642, dated Aug. 2, 2007.

International Search Report for PCT/US2011/043290, dated Dec. 9, 2011.

Irvine, D., et al., "DNA Integrity in Human Spermatozoa: Relationships with Semen Quality," Journal of Andrology, 2000, vol. 21, No. 1, pp. 33-44.

Juncosa, B., "DNA on the Loose: Next-Gen Blood Tests Tap Free-Floating Genetic Material," Scientific American, 2009, total 5 pages.

Jylhava, J., et al., "Aging is associated with quantitative and qualitative changes in circulating cell-free DNA: the Vitality 90+ study," Mechanisms of Ageing and Development, 2011, vol. 132, Issues 1-2, pp. 20-26.

Kadioglu, E., et al., "Detection of oxidative DNA damage in lymphocytes of patients with Alzheimer's disease," Biomarkers, 2004, vol. 9, Issue 2, pp. 203-209.

Kagan, V.E., et al., "Toward Mechanism-based Antioxidant Interventions," Annals of the New York Academy of Sciences, 2002, vol. 959, pp. 188-198.

Kalandarishvili, F., "Nakoplenie spontanno povrezhdennoj DNK v ne-i postgepatjektomirovannoj pecheni u staryh krys," Med. Novosti Gruzii, No. 5, pp. 11-12, 1998 (Reference in Russian and English-language translation).

Kaprin, et al., "Prognoz i lechenie bol'nih poverhnostnim rakom mochevogo puziria visokoi stepeni riska, Visokie Tehnologii v Onkologii," Rostov-na-Donu, vol. 3, pp. 149-150, 2000 (Reference in Russian and English-language translation).

Kawane, K., et at, "DNAse II Deficiency Causes Chronic Polyarthritis in Mice," Nature Clinical Practice Rheumatology, 2007, vol. 3, pp. 192.

Kenyon, C., "A Conserved Regulatory System for Aging", Cell, 2001, vol. 105, pp. 165-168.

Krapf, F., et al., "The Estimation of Circulating Immune Complexes, C3d, and Anti-ds-DNA-Antibody Serum Levels in the Monitoring of Therapeutic Plasmapheresis in a Patient with Systemic Lupus Erythematosus: A Case Report," Clinical and Experimental Rheumatology, 1985, vol. 3, No. 2, pp. 159-162.

Communication (Extended European Search report) issued by the Europe Patent Office in European application No. 15907392.3 dated May 24, 2019, 8 pages total.

Li, D., "DNase I Treatment Reduces GVHD in Mice. Biology of Blood and Marrow Transplantation" (2015) vol. 21, Issue 2, p. S339.

Demers M. at al., "Cancers predispose neutrophils to release extracellular DNA traps that contribute to cancer-associated thrombosis" PNAS (2012) vol. 109, No. 32, pp. 13076-13081.

Esposito, S. et al., "The Place of Desoxyribonuclease in the Treatment of Chronic Lymphatic Leukemia" Database EMBASE, Elsevier Science Publishers (1972) 1 page total.

(56) References Cited

OTHER PUBLICATIONS

Wen, F. et al., "Extracellular DNA in Pancreatic Cancer Promotes Cell Invasion and Metastasis" Cancer Res. (2013) vol. 73, pp. 4256-4266.
International Preliminary Report on Patentability issued by the International Searching Authority in International Application No. PCT/RU2015/000721, dated May 1, 2018, 5 pages total.
Mittal, B. et al., "Effect of Recombinant Human Deoxyriboneclease on Oropharyngeal Secretions in Patients with Head-and-Neck Cancers Treated with Radiochemotherapy" International Journal of Radiation Onocology Bioloy Physics (2013) vol. 87, No. 2, pp. 282-289.
Sawyers C.L., "The cancer biomarker problem" Nature (2008) vol. 452, No. 7187, pp. 548-552.
Song, L. et al., "NLRP3 Inflammasome in Neurological Diseases, from Functions to Therapies" Front. Cell. Neurosci. (2017) vol. 11, Article 63, pp. 1-17.
Tohme, S. et al., "Neutrophil Extracellular Traps Promote the Development and Progression of Liver Metastases after Surgical Stress" Cancer Res., Mar. 15, 2016, 76(6): 1367-1380.
Anunobi, R. et al., "Extracellular DNA Promotes Colorectal Tumor Cell Survival after Cytotoxic Chemotherapy" Journal of Surgical Research (2018) vol. 226, pp. 181-191.
Foote, M., "The Importance of Planned Dose of Chemotherapy on Time: Do We Need to Change our Clinical Practice?" The Oncologist: Physician Education (1998) vol. 3, pp. 365-368.
Lelbach, A. et al., "Current Perspectives of Catabolic Mediators of Cancer Cachexia" Med Sci Monit (2007) vol. 13, No. 9, pp. RA168-173.
Meirovitz, A. et al., "Novel Formation of Rnase and DNAse Employing Unique Nanospheres to Allow Oral Drug Delivery and Demonstrate Anticancer Activity" ASCO University (2015) Abstract, 2 pages total.
Mittra, I. et al., "Prevention of Chemotherapy Toxicity by Agents that Neutralize or Degrade Cell-Free Chromatin" Annals of Oncology (2017) vol. 28, pp. 2119-2127.
Petruzzelli, M. et al., "Mechanisms of Metabolic Dysfunction in Cancer-Associated Cachexia" Genes & Development (2016) vol. 30, pp. 489-501.
Kanyshkova, TG et al., "Multiple enzymic activities of human milk lactoferrin" European Journal of Biochemistry (2003) vol. 270, No. 16, pp. 3353-3361.
Communication (Japanese Notice of Grounds for Rejection) issued by the Japanese Patent Office in Japanese Application No. 2018-519282, dated Jun. 27, 2019, 9 pages total.
Schwarzenbach H. et al., "Detection and monitoring of cell-free DNA in blood of patients with colorectal cancer" Ann. N.Y. Acad. Sci., 2008, 1137:190-196.
Patutina, O. et al., Inhibition of metastasis development by daily administration of ultralow doses of RNase A and DNase I. Biochimie., Apr. 2011, 93(4): 689-96.
García-Olmo D.C. and García-Olmo, D. "Biological role of cell-free nucleic acids in cancer: the theory of genometastasis" Crit Rev Oncolog., 2013, 18:153-161.
Sergeeva, L. M., "Kliniko-laboratonaya otsenka mukoliticheskogo effekta pulmozima u bolnykh mukovistsidozom," Ekaterinburg, 1999, PhD dissertation in medicine, (Reference in Russian and English Translation).
Shah, P.L., et al., "Medium Term Treatment of Stable Stage Cystic Fibrosis with Recombinant Human Dnase I," Thorax, 1995, vol. 50, pp. 333-338.
Shak, S., et al., "Recombinant Human DNAse I Reduces the Viscosity of Cystic Fibrosis Sputum," Proc. Natl. Acad. Sci. USA, 1990, vol. 87, pp. 9188-9192.
Sherry, S., et al., "Presence and Significance of Desoxyribose Nucleoprotein in the Purulent Pleural Exudates of Patients," Experiemtnal Biology and Medicine, 1948, vol. 68, Issue 1, pp. 179-184.
Shevchuk, N.A., Vremyarazreshenniy Immunofluorescentniy Analiz na DNK i Issledovanie Soderzhaniya DNK v Syvoroike Cheloveka, Voprosi Medicinskoi Khimii, No. 4, 2001 (Reference in Russian and English Translation).
Shimony, A., et al., "Cell Free DNA Detected by a Novel Method in Acute ST-Elevation Myocardial Infarction Patients," Acute Cardiac Care, 2010, vol. 12, Issue 3, pp. 109-111.
Shuster, A.M., et al., "DNA Hydrolyzing Autoantibodies," Science, 1992, vol. 256, Issue 5057, pp. 665-667.
SIGMA Product Information Sheet for Deoxyribonuclease I from Bovine Pancreas, 2006.
Simpson, G., et al., "Successful Treatment of Empyema Thoracis with Human Recombinant Deoxyribonuclease," Thorax, 2003, vol. 58, No. 4, pp. 365-366.
Sugihara, S., et al., "Deoxyribonuclease Treatment Prevents Blood-Borne Liver Metastasis of Cutaneously Transplanted Tumour Cells in Mice," British Journal of Cancer, 1993, vol. 67, No. 1, pp. 66-70.
Tetz, G.V., et al., "Effect of DNase and Antibiotics on Biofilm Characteristics," Antimicrobial Agents and Chemotherapy, 2009, vol. 53, No. 3, pp. 1204-1209.
Tetz, GV, et al., "Effect of Nucleolytic, Proteolytic, and Lipolytic Enzymes on Transfer of Antibiotic Resistance Genes in Mixed Bacterial Communities," Universal Journal of Medicine and Dentistry, 2012, vol. 1, No. 4, pp. 46-50.
Tetz, V.V., et al., "Effect of Extracellular DNA Destruction by DNase I on Characteristics of Forming Biofilms," DNA and Cell Biology, 2010, vol. 29, No. 8, pp. 399-405.
Tolkoff-Rubin, N.E., et al., "Recent Advances in the Diagnosis and Management of Infection in the Organ Transplant Receipient," Seminars of Nephrology, 2000, vol. 20, No. 2, pp. 148-163.
Treshalin, I.D., et al., "Modification of antitumor drugs toxicity as a method of enhancing anticancer chemotherapeutic efficacy," Possiiskii bioterapevticheskii zhumal, 2005, tom 4, No. 3, pp. 87-94.
Ulrich, R., et al., "Toxicogenomics and Drug Discovery: Will New Technologies Help us Produce Better Drugs?," Nature, 2002, vol. 1, pp. 84-88.
Van Der Vaart, M., et al., "A Method of Characterization of Total Circulating DNA," Annals of the New York Academy of Sciences, 2008, vol. 1137, pp. 92-97.
Varidase Buccal Tablets product information from Lederle Laboratories Inc., Canad. M. A. J., 1961, vol. 84, pp. 867-868.
Varidase product information from EPGOnline, accessed on Dec. 12, 2011, total 2 pages.
Vijg, J., "Somatic Mutations, Genome Mosaicism, Cancer and Aging," Current Opinion in Genetics & Development, 2014, vol. 26, pp. 141-149.
Vonmoos, P.L., et al., "Absorption and Hematologic Effect of Streptokinase-Streptodomase (varidase) After Intracavital or Oral Administration," Schweiz Med Wochenschr, 1979, vol. 109, pp. 1538-1544, Abstract.
Whitchurch, C.B., et al., "Extracellular DNA Required for Bacterial Biofilm Formation," Science, 2002, vol. 295, Issue 5559, pp. 1487.
Whitfield, J.F., et al., "The Effects of X-Radiation on Lactate Metabolism of Mammalian Cells," Experiemental Cell Research, 1964, vol. 37, Issue 3, pp. 637-649.
WHO Laboratory Manual for the Examination of Human Semen and Sperm-cervical Mucus Interaction, 4th ed., Cambridge University Press, 1999, pp. 128.
Written Opinion issued International Application No. PCT/RU2015/000721 dated Aug. 18, 2016, 4 pages.
Written Opinion issued International Application No. PCT/RU2016/000284 dated Oct. 7, 2016, 5 pages.
Yastrebova / Yaserova N.E., "Razrabotka I Izuchenie diagnosticheskikh vozmozhnostei immunofermentnykh test-sistem na osnove antigennykh preparatov zolotistogo stafilokokka I Dnk," Avtoreferat dissertatsii na soiskanie uchenoi stepeni kandidata meditsinskikh nauk (author's abstract of PhD thesis in medical sciences), M., 1988, pp. 17-18, (Reference in Russian and English language translation).
Yasuda, T., et al., "Activity Measurement for Deoxyribonucleases I and II with Picogram Sensitivity Based on DNALSYBR Green I Fluorescence," Analytical Biochemistry, 1998, vol. 255, Issue 2, pp. 274-276.

(56) References Cited

OTHER PUBLICATIONS

Ye, L., et al., "Quantification of Circulating Cell-Free DNA in the Serum of Patients with Obstructive Sleep Apnea-Hypopnea Syndrome," Lung, 2010, vol. 188, Issue 6, pp. 469-474.

Youssoufian, H., et al., "Mechanisms and Consequences of Somatic Mosaicism in Humans," Nature Reviews Genetics, 2002, vol. 3, pp. 748-758.

Zaman, S., et al., "Direct Amplification of Entamoeba Histolytica DNA from Amoebic Liver Abscess Pus Using Polymerase Chain Reaction," Parasitology Research, 2000, vol. 86, Issue 9, pp. 724-728.

Zaravinos, A., et al., "Levosimendan Reduces Plasma Cell-Free DNA Levels in Patients with Ischemic Cardiomyopathy," J. Thromb. Thrombolysis, 2011, vol. 31, pp. 180-187.

Zhong, S., et al., "Presence of Mitochondrial tRNA(leu(UUR) A to G 3243 Mutation in DNA Extracted from Serum and Plasma of Patients with Type 2 Diabetes Mellitus," Journal of Clinical Pathology, 2000, vol. 53, pp. 466-469.

Amendment filed in U.S. Appl. No. 10/619,356 dated Jun. 24, 2008.

Communication issued in European Search Report for European Patent Appl. No. EP04775224, dated Jul. 5, 2011.

Communication issued in European Search Report for European Patent Appl. No. EP047489554, dated May 23, 2011.

Krtolica, A. et al., "Senescent Fibroblasts Promote Epithelial Cell Growth and Tumorigenesis: A Link Between Cancer and Aging," PNAS, 2001, vol. 98, No. 21, pp. 12072-12077.

Lachmann, P.J., "Lupus and Desoxyribonuclease," Lupus, 2003, vol. 12, vol. 12, pp. 202-206.

Lecompte, T. et al., "Detection of Free-Circulating Tumor-Associated DNA in Plasma of Colorectal Cancer Patients and its Association with Prognosis," International Journal of Cancer, 2002, vol. 100, Issue 5, pp. 542-548.

Lee, D., "Continued Marketing of a Useless Drug ('Varidase') in Panama," Lancet, 1990, vol. 335, pp. 667.

Leland, P.A., et al., "Cancer Chemotherapy—Ribonucleases to the Rescue," Chemistry & Biology, 2001, vol. 8, pp. 405-413.

Leon et al., "Free DNA in the Serum of Cancer Patients and the Effect of Therapy," Cancer Research, vol. 37, pp. 646-650, 1977.

Li, X. et al., "Systemic Diseases Caused by Oral Infection," Clinical Microbiology Reviews, 2000, vol. 13, No. 4, pp. 547-558.

Liggett, T. et al., "Methylation Patterns of Cell-Free Plasma DNA in Relapsing-Remitting Multiple Sclerosis," Journal of Neurological Sciences, 2010, vol. 290, pp. 16-21.

Macanovic, M. et al., "The Treatment of Systemic Lupus-Erythematosus (SLE) in NZB/W FI-Hybrid Mice-Studies with Recombinant Murine DNase and with Dexamethasone," Clinical and Experimental Immunology, 1996, vol. 106, pp. 243-252.

Malickova, K. et al., "Decreased Activity of DNase-I Predisposes to Immune-Mediated Complications in IBD Patients During Anti-TNFA Treatment," Gastroenterology, 2010, Abstract 202, vol. 138 (5 Supplement 1), pp. S-37.

Martinod, K. et al., "Peptidylarginine Deiminase 4 Promotes Age-Related Organ Fibrosis," Journal of Experimental Medicine, 2017, vol. 214, No. 2, pp. 439-458.

Maurer, H.R. "Bromelain: Biochemistry, Pharmacology and Medical Use," Cellular and Molecular Life Sciences, 2001, vol. 58, pp. 1234-1245.

Mel'Nikov, D. et al., "Voprosy onkologicheskoi pomoschi na etape reformirovaniya zdravookhraneniya," Ekaterinburg, 1996, pp. 159-161 (Reference in Russian and English-language translation).

Merkus, P.J.F.M. et al., "DNase Treatment for Atelectasis in Infants with Severe Respiratory Syncytial Virus Bronchiolitis," European Respiratory Journal, 2001, vol. 18, pp. 734-737.

Moghadasian, M.H. et al., "A Safety Look at Currently Available Statins," Expert Opinion on Drug Safety, 2002, vol. 1, Issue 3, pp. 269-274.

Moreira, V.G. et al., "Usefulness of Cell-Free Plasma DNA, Procalcitonin and C-Reactive Protein as Markers of Infection in Febrile Patients," Annals of Clinical Biochemistry, 2010, vol. 47, pp. 253-258.

Morton, C.O. et al., "Dynamics of Extracellular Release of Aspergillus Fumigatus DNA and Galactomannan During Growth in Blood and Serum," Journal of Medical Microbiology, 2010, vol. 59, pp. 408-413.

Mosca, M. et al., "Cell-Free DNA in the Plasma of Patients with Systemic Sclerosis," Clinical Rheumatology, 2009, vol. 28, pp. 1437-1440.

Mueller, G.M., "Fungal Biodiversity: What Do We Know? What Can We Predict?," Biodiversity and Conservation, 2007, vol. 16, Issue 1, pp. 1-5.

Mutirangura, A., "Serum/Plasma Viral DNA: Mechanisms and Diagnostic Applications to Nasopharyngeal an Cervical Carcinoma," Annals of the New York Academy of Sciences, 2001, vol. 945, pp. 59-67.

National Institute On Aging, "Can We Prevent Aging? Tips from the National Institute on Aging," 2012, pp. 1-8.

Nestle, M. et al., "An Extracellular Nuclease from Serratia Marcescens," Journal of Biological Chemistry, 1969, vol. 244, No. 19, pp. 5213-5218.

Ngan, R.K.C. et al., "Remarkable Application of Serum EBV EBER-1 in Monitoring Response of Nasopharyngeal Cancer Patients to Salvage Chemotherapy," Annals New York Academy of Sciences, 2001, vol. 945, pp. 73-79.

Oliven, A. et al., "Orally and Rectally Administered Streptokinase," Pharmacology, 1981, vol. 22, pp. 135-138.

Osivac, et al., "Reorganizacija DNK i biologicheskoje starenije," Biohimija, 1997, vol. 62, pp. 1491-1502, (Reference in Russian and English-language translation).

Parrinello, S. et al., "Stromal-Epithelial Interactions in Aging and Cancer: Senescent Fibroblasts alter Epithelial Cell Differentiation," Journal of Cell Science, 2004, vol. 118, No. 3, pp. 485-496.

Perel'Man, M.I. et al., "Molekuljarnaj a medicina i lechenie tuberkuleza," Problemi tuberkuleza, No. 5, pp. 5-7, 2001 (Reference in Russian and English-language translation).

Perl, T.M., "The Threat of Vancomycin Resistance," The American Journal of Medicine, 1999, vol. 106, Issue 5, pp. 26s-37s.

Pietropaolo, M. et al., "Evidence of Islet Cell Autoimmunity in Elderly Patients with Type 2 Diabetes," Diabetes, 2000, vol. 49, pp. 32-38.

Pressler, T., "Review of Recombinant Human Deoxyribonuclease (rhDNase) in the Management of Patients with Cystic Fibrosis," Biologics: Targets & Therapy, 2008, vol. 2, No. 4, pp. 611-617.

Prince, W.S. et al, "Pharmacodynamics of Recombinant Human DNase I in Serum," Clin Exp Immunol, 1998, vol. 113, pp. 289-296.

Pulmozyme® (dornase alfa) Inhalation Solution product leaflet, Genetech, Inc., 2005.

Raz, E. et al., "Anti-DNA antibodies bind directly to renal antigens and induce kidney dysfunction in the isolated perfused rat kidney," J. Immunol., 1989, vol. 142, No. 9, pp. 3076-3082.

Riches, A.C. et al., "Blood Volume Determination in the Mouse," Journal of Physiology, 1973, vol. 228, Issue 2, pp. 279-284.

Robertson, D. et al., "The Microbiology of the Acute Dental Abscess," Journal of medical Microbiology, 2009, vol. 58, pp. 155-162.

Roche, Pulmozyme®, Dornase alfa solution for inhalation 1.0 mg/ml, Data Sheet, 2008.

Roper, N.A., "Cause-Specific Mortality in a Population with Diabetes: South Tees Diabetes Mortality Study," Diabetes Care, 2002, vol. 25, No. 1, pp. 43-48.

Ross, K.A., "Evidence of Somatic Gene Conversion and Deletion in Bipolar Disorder, Crohn's Disease, Coronary Artery Disease, Hypertension, Rheumatoid Arthritis, Type-1 Diabetes, and Type-2 Diabetes," BMC Medicine, 2011, vol. 9, No. 12, pp. 1-29.

Rowe, P. et al., "WHO Manual for the Standardized Investigation and Diagnosis of the Infertile Couple," Cambridge University Press, 1993, pp. 83.

Rowlatt, C. et al., "Lifespan, Age Changes and Tumour Incidence in an Ageing C57BL Mouse Colony," Laboratory Animals, 1976, vol. 10, pp. 419-442.

Schapira, A.H.V., "Mitochondrial disease," Lancet, 2006, vol. 368, pp. 70-82.

Schloss, P.D. et al., "Status of the Microbial Census," Microbiology and Molecular Biology Reviews, 2004, vol. 68, No. 4, pp. 686-691.

(56) References Cited

OTHER PUBLICATIONS

Schmitz, K.H. et al., "The Intersection of Cancer and Aging: Establishing the Need for Breast Cancer Rehabilitation," Cancer Epidemiology, Biomarkers & Prevention, 2007, vol. 16, No. 5, pp. 866-872.
Scoble, J.E. et al., "Athersclerotic Renovascular Disease Causing Renal Impairment—A Case for Treatment," Clinical Nephrology, 1989, vol. 31, No. 3, pp. 119-122.
Sefton, A.M., "Mechanisms of Antimicrobial Resistance," Drugs, 2002, vol. 62, Issue 4, pp. 557-566.
Amendment filed in U.S. Appl. No. 10/564,861 dated Jun. 24, 2008.
Anderson, G.P., et al., "Acquired Somatic Mutations in the molecular Pathogenesis of COPD," Trends in Pharmacological Sciences, 2003, vol. 24, Issue 2, pp. 71-76.
Andreassi, M.G., "Coronary Atherosclerosis and Somatic Mutations: An Overview of the Contributive Factors for Oxidative DNA Damage," Mutation Research, 2003, vol. 543, Issue 1, pp. 67-86.
Anker, P., et al., "Tumor-related Alterations in Circulating DNA, Potential for Diagnosis, Prognosis and Detection of Minimal Residual Disease," Leukemia, 2001, vol. 15, No. 2, pp. 289-291.
Arinchina, N.I., et al., "Cellular and Humoral Mechanisms of Immunity Changing," 1982, pp. 280-282.
Ashton, G., "Growing Pains for Biopharmaceuticals," Nature Biotechnology, 2001, vol. 19, pp. 307-311.
Aung, K.L., et al., "Current Status and Future Potential of Somatic Mutation Testing from Circulating Free DNA in Patients with Solid Tumours," HUGO Journal, 2010, vol. 4, No. 1-4, pp. 11-21.
Barrett, J.P., et al., "A Systematic Review of the Antifungal Effectiveness and Tolerability of Amphotericin B Formulations," Clinical Therapeutics, 2003, vol. 25, Issue 5, pp. 1295-1320.
Beckman, J.A., et al., "Diabetes and Atherosclerosis: Epidemiology, Pathophysiology, and Management," JAMA, 2002, vol. 287, No. 19, pp. 2570-2581.
Beishon, M., "What Can We Learn from Liquid Biopsies? Early Detection, Disease Prognosis, A Guide to Treatment, A Key to Unlocak the Secrets of How Cancers Evolve. Researchers have High Hopes for What They Can Learn from the Biological Detritus Shed by Primary Tumours and Metastases," CancerWorld, 2015, No. 68, pp. 12-17.
Bertoni, A.G., et al., "Diabetes and the Risk of Infection-Related Mortality in the U.S.," Diabetes Care, 2001, vol. 6, Issue 6, pp. 1044-1049.
Botto, N., et al., "Elevated Levels of Oxidative DNA damage in Patients with Coronary Artery Disease," Coronary Artery Disease, 2002, vol. 13, No. 5, pp. 269-274.
Boyko, M., et al., "Cell-free DNA—A Marker to Predict Ischemic Brain Damage in a Rat Stroke Experimental Model," Journal of Neurosurgical Anesthesiology, 2011, vol. 23, No. 3, pp. 222-228.
Burt, M., et al., "Detection of Circulating Donor Deoxyribonucleic Acid By Microsatellite Analysis in a Liver Transplant Recipient," Liver Transplantation and Surgery, 1996, vol. 2, No. 5, pp. 391-394.
Campisi, J., "Cancer and Ageing: Rival Demons?," Nature Reviews Cancer, 2003, vol. 3, pp. 339-349.
Campisi, J., et al., "Cellular Senescence: When Bad Things Happen to Good Cells," Nature Reviews, 2007, vol. 8, pp. 729-740.
Canudas-Romo, V., "Three Measures of Longevity: Time Trends and Record Values," Demography, 2010; vol. 47, Issue 2, pp. 299-312.
Canuto, M.M., et al., "Antifungal Drug Resistance to Azoles and Polyenes," Lancet Infectious Dieases, 2002, vol. 2, No. 9, pp. 550-563.
Cizman, M., "The Use and Resistance of Antibiotics in the Community," International Journal of Antimicrobial Agents, 2003, vol. 21, Issue 4, pp. 297-307.
Clearfield, M.B., "Statins: Balancing Benefits, Efficacy and Safety," Expert Opinion on Pharmacotherapy, 2002, vol. 3, Issue 5, pp. 469-477.
Communication European Office Action, dated Jun. 12, 2013, which issued during the prosecution of European Patent Application No. 05745412.6, which corresponds to the present application.
Communication Extended European Search Report for European Patent Appl. No. EP12170750 dated Aug. 3, 2012.
Communication Extended European Search Report for European Patent Appl. No. EP12170754 dated Aug. 3, 2012.
Communication Extended European Search Report for European Patent Appl. No. EP12170757 dated Aug. 3, 2012.
Communication issued by the European Patent Office in European Application No. 04 775 224.1, dated Jul. 22, 2010.
Communication issued by the European Patent Office in European Application No. 04748955.4, dated Jan. 11, 2011.
Communication issued by the European Patent Office in European Application No. 04748955.4, dated May 21, 2010.
Communication issued by the Japanese Patent Office in Japanese Application No. 2009-539202, dated Feb. 22, 2013.
Communication issued by the Japanese Patent Office in Japanese Application No. 2009-539202, dated Mar. 13, 2012.
Communication Supplementary European Search Report for European Patent Appl. No. EP03796243, dated Jan. 12, 2010.
Communication Supplementary European Search Report for European Patent Appl. No. EP04748955, dated May 19, 2009.
Communication Supplementary European Search Report for European Patent Appl. No. EP04775224, dated Oct. 28, 2009.
Communication Supplementary European Search Report for European Patent Appl. No. EP05745412, dated Jul. 10, 2009.
Communication Supplementary European Search Report for European Patent Appl. No. EP06843990, dated Nov. 23, 2009 and cf Form 1507.
Communication Translation of International Preliminary Report on Patentability for PCT/RU2003/000304, dated Nov. 1, 2005.
Communication Translation of International Preliminary Report on Patentability for PCT/RU2004/000260, dated Jan. 14, 2006.
Communication Translation of International Preliminary Report on Patentability for PCT/RU2004/000261, dated Dec. 2, 2005.
Communication Translation of International Preliminary Report on Patentability for PCT/RU2004/000262, dated Apr. 12, 2006.
Communication Translation of International Preliminary Report on Patentability for PCT/RU2005/000236, dated Feb. 13, 2008.
Communication Translation of International Preliminary Report on Patentability for PCT/RU2006/000642, dated Jul. 7, 2009.
Coppe, J-P., et al., "Secretion of Vascular Endothelial Growth Factor by Primary Human Fibroblasts at Senescence," Journal of Biological Chemistry, 2006, vol. 281, No. 40, pp. 29568-29574.
Davis, B.R., et al., "Somatic Mosaicism in the Wiskott-Aldrich Syndrome: molecular and Functional Characterization of Genotypic Revetants," Clinical Immunology, 2010, vol. 135, pp. 72-83.
Davis, J.C., et al., "Recombinant Human Dnase I (rhDNase) in Patients with Lupus Nephritis," LUPUS, 1999, vol. 8, Issue 1, pp. 68-76.
Dayan, A.D., "Forward: Pharmacological-Toxicological (Expert Report on Recombinant Human Deoxyribonuclease I (rhDNase; PulmozymeTm))," Human and Experimental Toxicology, 1994, vol. 3:S2, pp. 41 pages total.
Deitsch, K.W., et al., "Transformation of Malaria Parasites by the Spontaneous Uptake and Expression of DNA from Human Erythrocytes," Nucleic Acids Research, 2001, vol. 29, No. 3, pp. 850-853.
Deocharan B., et al., "Alpha-Actinin is a Cross-Reactive Renal Target for Pathogenic Anti-DNA Antibodies," Journal of Immunology, 2002, vol. 168, pp. 3072-3078.
Department of Health and Human Services Food and Drug Administration, Federal Register, Dec. 13, 1985, vol. 50, No. 240.
Dewitt, D.E., et al., "Outpatient Insulin Therapy in Type 1 and Type 2 Diabetes Mellitus: Scientific Review," JAMA, 2003, vol. 289, No. 17, pp. 2254-2264.
Dittmar, M., et al., "A Novel Mutation in the DNASE1 Gene is Related with Protein Instability and Decreased Enzyme Activity in Thyroid Autoimmunity," Journal of Autoimmunity, 2009, vol. 32, pp. 7-13.
El Hassan, N.O., et al., "Rescue Use of Dnase in Critical Lung Atelectasis Mucus Retention in Premature Neonates," Pediatrics., 2001, vol. 108, pp. 468-470.
Communication (Japanese Notice of Grounds for Rejection) issued by the Japanese Patent Office in Japanese Application No. 2018-519282, dated Apr. 23, 2020, 6 pages total.

(56) References Cited

OTHER PUBLICATIONS

Smalheiser, N.R., "Mining Clinical Case Reports to Identify New Lines of Investigation in Alzheimer's Disease: The Curious Case of DNase I" Journal of Alzheimer's Disease Reports (2019) vol. 3, pp. 71-76.
Weintraub, K., "Tau Shows Promis as Achilles' Heel for Alzheimer's and Similar Diseases" Neurological Health (2020) (available at https://www.scientificamerican.com/article/tau-shows-promise-as-achilles-heel-for-alzheimers-and-similar-diseases/), 9 pages total.
Fani, L. et al., "Helicobacter Pylori and the Risk of Dementia: A Population-Based Study" Alzheimer's & Dementia (2018) vol. 14, pp. 1377-1382.
Gieffers, J. et al., "Failure to Detect Chlamydia Pneumoniae in Brain Sections of Alzheimer's Disease Patients" Journal of Clinical Microbiology (2000) vol. 38, No. 2, pp. 881-882.
Li, W. et al., "Helicobacter Pylori Infection is a Potential Protective Factor Against Conventional Multiple Sclerosis in the Japanese Population" Journal of Communication (2007) vol. 184, pp. 227-231.
Marques, A.R. et al., "Lack of Evidence of Borrelia Involvement in Alzheimer's Disease" Journal of Infectious Diseases: To the Editor (2000) vol. 182, pp. 1006-1007.
Nicolson, G.I. et al., "Role of Chronic Bacterial and Viral Infection in Neurodegenerative, Neurobehavioural, Psychiatric, Autoimmune and Fatiguing Illnesses: Part 2" British Journal of Medical Practitioners (2010) vol. 3, No. 1, pp. 24-33.
Ring, R.H. et al., "Failure to Detect Chlamydia Pneumoniae in the Late-Onset Alzheimer's Brain" Journal of Clinical Microbiology (2000) vol. 38, No. 7, pp. 2591-2594.
Scalzo, P.L. et al., "Quantitative Plasma DNA Analysis in Parkinson's Disease" Neuroscience Letters (2009) vol. 452, pp. 5-7.
Taylor, G.S. et al., "Failure to Correlate C. Pneumoniae with Late Onset Alzheimer's Disease" Neurology (2002) vol. 59, pp. 142-143.
Yao, G. et al., "Meta-Anaylsis of Association Between Helicobacter Pylori Infection an Multiple Sclerosis" Neuroscience Letters (2016) vol. 620, pp. 1-7.
Migliore L., et al., Oxidative DNA damage in peripheral leukocytes of mild cognitive impairment and AD patients. Neurobiol Aging. May 2005; 26(5):567-73.
Victor Tetz et al. Effect of deoxyribonuclease I treatment for dementia in end-stage Alzheimer's disease: a case report. Journal of Medical Case Reports. vol. 10, No. 1, May 28, 2016.
Meng H. et al, "Clinical Application of Polysialylated Deoxyribonuclease and Erythropoietin" Recent Patents on Drug Delivery and Formulation, 2018, vol. 12, pp. 212-222.
Colella, P. et al., "AAV Gene Transfer with Tandem Promoter Design Prevents Anti-Transgene Immunity and Provides Persistent Efficacy in Neonate Pompe Mice" Methods & Clinical Development (2019) vol. 12, pp. 85-101.
Communication (International Preliminary Report on Patentability) mailed in International Application No. PCT/RU2019/050003 dated Jul. 21, 2020, 8 pages total.
Communication (International Search Report) mailed in International Application No. PCT/RU2019/050003 dated May 7, 2019, 4 pages total.
Communication (Written Opinion) mailed in International Application No. PCT/RU2019/050003 dated May 7, 2019, 7 pages total.
Communication (International Search Report) mailed in International Application No. PCT/US2020/41574 dated Dec. 18, 2020, 7 pages total.
Communication (International Search Report) mailed in International Application No. PCT/US2020/41579 dated Dec. 22, 2020, 6 pages total.
Communication (Written Opinion) mailed in International Application No. PCT/US2020/41574 dated Dec. 18, 2020, 11 pages total.
Communication (Written Opinion) mailed in International Application No. PCT/US2020/41579 dated Dec. 22, 2020, 8 pages total.

* cited by examiner

EXTRACELLULAR DNA AS A THERAPEUTIC TARGET IN NEURODEGENERATION

CROSS-REFERENCE TO RELATED APPLICATIONS

This application is a U.S. National Phase of International Application No. PCT/RU2016/000284, filed May 11, 2016, which was published as WO 2016/190780 A1 on Dec. 1, 2016, and claims priority to U.S. Provisional Application No. 62/165,255, filed on May 22, 2015, the disclosures of which are herein incorporated by reference in their entireties.

SEQUENCE LISTING

The instant application contains a Sequence Listing which has been submitted in ASCII format via EFS-Web and is hereby incorporated by reference in its entirety. Said ASCII copy, created on Jul. 5, 2018, is named 15576611_seqlist_ST25.txt and is 1,518 bytes in size.

FIELD OF THE INVENTION

The invention relates to the use of deoxyribonuclease (DNase) enzyme for inhibiting progression and for prevention and treatment of neurodegeneration.

BACKGROUND OF THE INVENTION

Neurodegeneration is a separate clinical pathological condition with progressive loss of structure and/or function of neurons, including death of neurons. Molecular pathways leading to neurodegeneration are highly disease-specific (e.g., accumulation of abnormally folded amyloid-beta and tau proteins in the brain in Alzheimer's disease patients; accumulation of alpha-synuclein in Parkinson's disease; accumulation of mutant Huntingtin in Huntington's disease; accumulation of TDP-43 and FUS protein aggregates in Amyelotropic Lateral Sclerosis (ALS); accumulation of mitochondrial DNA mutations and broken mitochondria division mechanics in aging) and result in neuronal cell death at advanced stages of disease progression. Programmed cell death including apoptosis seems to play a key role in the progression of neurodegeneration at late disease stage, as demonstrated by studies on animal models and cell lines (Radi E., et al., J Alzheimers Dis. 2014; 42).

Diseases involving clinical signs related to neurodegeneration affect almost 30 million individuals and lead to disability and death. Neurodegeneration usually leads to progressive nervous system dysfunction and is often associated with atrophy of the affected central or peripheral structures of the nervous system. Neurodegeneration is associated with a large group of neurological conditions with heterogeneous clinical and pathological expressions affecting specific subsets of neurons in specific functional anatomic systems. The non-limiting list of disorders where neurodegeneration has a significant impact on clinical and pathological picture is presented below:

Alzheimer's disease
Senile dementia of the Alzheimer type
Pick's disease (lobar atrophy)
Huntington's disease
Multiple system atrophy combining dementia with ataxia and/or manifestations of Parkinson's disease
Progressive supranuclear palsy (Steel-Richardson-Olszewski)
Diffuse Lewy body disease
Corticodentatonigral degeneration
Hallervorden-Spatz disease
Progressive familial myoclonic epilepsy
Paralysis agitans (Parkinson's disease)
Striatonigral degeneration
Progressive supranuclear palsy
Torsion dystonia (torsion spasm; dystonia musculorum deformans)
Spasmodic torticollis and other dyskinesis
Familial tremor
Gilles de la Tourette syndrome
Cerebellar cortical degeneration
Olivopontocerebellar atrophy (OPCA)
Spinocerebellar degeneration (Friedreich's ataxia and related disorders)
Syndrome of central autonomic nervous system failure (Shy-Drager syndrome)
Amyotrophic lateral sclerosis
Spinal muscular atrophy
Primary lateral sclerosis
Hereditary spastic paraplegia
Peroneal muscular atrophy (Charcot-Marie-Tooth)
Hypertrophic interstitial polyneuropathy (Dejerine-Sottas)
Miscellaneous forms of chronic progressive neuropathy
Pigmentary degeneration of the retina (retinitis pigmentosa)
Hereditary optic atrophy (Leber's disease)
Bipolar disorder
Epilepsy
Migraine
Schizophrenia.

Traditionally, searches for new therapeutic modalities for neurodegeneration were focused on modulation of molecular pathways inside neuronal cells in order to prevent neuronal cell death and improve neuronal cells functionality. The histone acetyltransferase activators (US 20150119466), cyclin-dependent protein kinase 5 inhibitors (US 20150119348), neurotrophin mimetics (US 20150111903), semaphorin-4D blockers (US 20150110800), microsomal prostaglandin E synthase-1 inhibitors (US 20150087646), N-methyl-d-aspartate (NMDA) receptor inhibitors were proposed as agents useful in treatment of neurodegenerative disorders. NMDA receptor inhibitor memantine has been used clinically for treatment of many neurodegenerative disorders, including Alzheimer's disease, amyotrophic lateral sclerosis (ALS), Parkinson's and Huntington's diseases. Memantine also shows promise as a treatment for other diseases associated with excessive NMDA receptor activation in the central nervous system (CNS), including glaucoma, multiple sclerosis, epilepsy and neuropathic pain (J. Johnson et al., Current Opinion in Pharmacology, 2006, V6, pp. 61-67).

Circulating extracellular (also called "cell free") nucleic acids were discovered more than 60 years ago (Anker P., Circulating DNA in plasma or serum, Clin Chim Acta. 2001; 313(1-2): 143-6). DNA levels in normal plasma samples are quite low with concentrations varying from 3.6 to 5.0 ng/ml. Normal plasma samples mainly contain DNA fragments of about 180 bp and to a much smaller extent larger fragments (e.g., fragments of 500 bp or larger). Circulating extracellular DNA has been described as therapeutic target in several diseases and conditions, including cancer, infection, diabetes, delayed-type hypersensitivity, and fertility (see, e.g., U.S. Pat. Nos. 8,916,151; 8,871,200; 8,796,004; 8,710,012; 8,535,663; 8,431,123; 8,388,951; 7,612,032; PCT/IL2007/001250; PCT/IB2013/056321).

SUMMARY OF THE INVENTION

As specified in the Background Section, there is a great need in the art to develop new compositions and methods for treating neurodegeneration. The present invention addresses this and other needs by providing compositions and methods based on DNase enzyme.

Specifically, in one aspect, the invention provides a method for preventing, treating and/or inhibiting progression of neurodegeneration (e.g., primary neurodegeneration) in a patient in need thereof (e.g., a mammal such as human or an experimental animal model), comprising administering to said patient a therapeutically effective amount of a DNase enzyme.

In a related aspect, the invention provides a pharmaceutical composition comprising a DNase enzyme for use in preventing, treating and/or inhibiting progression of neurodegeneration (e.g., primary neurodegeneration).

In a further aspect, the invention provides a use of a DNase enzyme for preventing, treating and/or inhibiting progression of neurodegeneration in a patient in need thereof.

In one embodiment, the neurodegeneration is associated with an increased level of extracellular DNA (e.g., prokaryotic and/or human) in blood or cerebrospinal fluid or intestine of the patient, which level is higher than the control level (e.g., the level of extracellular DNA in blood or cerebrospinal fluid or intestine of a healthy age-matched individual or an average level of extracellular DNA in blood or cerebrospinal fluid or intestine of several healthy age-matched individuals). In one embodiment, the neurodegeneration is associated with a neurodegenerative disorder. Non-limiting examples of encompassed neurodegenerative disorders include, e.g., Alzheimer's disease (e.g., late-onset Alzheimer's disease), Parkinson's disease, Amyotrophic Lateral Sclerosis (ALS), and Huntington's disease. In one embodiment, the neurodegeneration is associated with a nervous system dysfunction such as, e.g., schizophrenia or bipolar disorder.

In one embodiment, the therapeutically effective amount of the DNase enzyme is sufficient to destroy said extracellular DNA (e.g., is sufficient to decrease the average molecular weight of said extracellular DNA [e.g., as measured by gel electrophoresis]) in blood or cerebrospinal fluid or intestine of the patient.

In one embodiment, said DNase is a recombinant DNase. In one embodiment, said DNase is DNase I. In one embodiment, said DNase has extended half-life (e.g., is conjugated with polysialic acid or is protected from binding to actin by modification of actin binding-site; see, e.g., Gibson et al., (1992) J. Immunol. Methods, 155, 249-256).

In one embodiment, said DNase is administered by intravenous, subcutaneous or intramuscular route. In one specific embodiment, said DNase is DNase I and is administered in the amount of at least 0.04 mg per kg per day or 0.05-10000 Kunitz units per kg per day during at least one day.

In another embodiment, said DNase is administered enterally (e.g., orally). In one specific embodiment, said DNase is DNase I and is administered in the amount of at least 0.04 mg per kg per day or 0.05-10000 Kunitz units per kg per day during at least one day.

In yet another embodiment, said DNase is administered into cerebrospinal fluid. In one specific embodiment, said DNase is DNase I and is administered in the amount of at least 0.1 mg per day.

These and other aspects of the present invention will be apparent to those of ordinary skill in the art in the following description, claims and drawings.

DETAILED DESCRIPTION OF THE INVENTION

Figure 1:
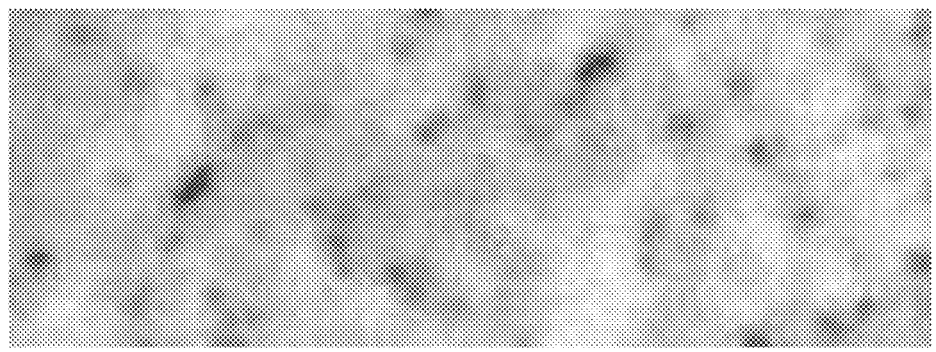
FIG. 1 shows accumulation of labeled extracellular DNA in rat brain parenchyma after its injection into carotid artery.

The present invention is based on an unexpected discovery that extracellular DNA (both eukaryotic and prokaryotic) is present in elevated levels in blood and cerebrospinal fluid (CSF) of patients suffering from neurodegeneration (e.g., neurodegeneration associated with Alzheimer's disease, Parkinson's disease, Amyotrophic Lateral Sclerosis, Huntington's disease, schizophrenia, and bipolar disorder) and that said extracellular DNA penetrates blood brain barrier (BBB) and exerts neuronal toxicity. As further demonstrated herein, the administration of DNase enzymes results in treatment/amelioration of neurodegeneration and is accompanied by the reduction of the level of circulating extracellular DNA.

Definitions

The term "neurodegeneration" is used herein to refer to a separate clinical pathological condition with progressive loss of structure and/or function of neurons, including death of neurons. The neurodegeneration can be primary or secondary. Non-limiting examples of diseases involving primary neurodegeneration include, e.g., Alzheimer's disease (AD), Mild Cognitive Impairment (MCI), Parkinson's disease (PD), Huntington's disease (HD), prion-caused diseases, frontotemporal dementia (FTD), Lewy body dementia, vascular dementias, Amyotrophic Later Sclerosis (ALS), chronic traumatic encephalopathy (CTE), progressive supranuclear palsy (PSP), multiple system atrophy (MSA), corticobasal degeneration (CBGD), Pick's disease, olivopontocerebellar atrophy (OPCA), senile dementia of the Alzheimer type, progressive supranuclear palsy (Steel-Richardson-Olszewski), corticodentatonigral degeneration, Hallervorden-Spatz disease, progressive familial myoclonic epilepsy, striatonigral degeneration, torsion dystonia (e.g., torsion spasm; dystonia musculorum deformans), spasmodic torticollis and other dyskinesis, familial tremor, Gilles de la Tourette syndrome, cerebellar cortical degeneration, spinocerebellar degeneration (e.g., Friedreich's ataxia and related disorders), Shy-Drager syndrome, spinal muscular atrophy, primary lateral sclerosis, hereditary spastic paraplegia, peroneal muscular atrophy (Charcot-Marie-Tooth), hypertrophic interstitial polyneuropathy (Dejerine-Sottas), chronic progressive neuropathy, pigmentary degeneration of the retina (retinitis pigmentosa), and hereditary optic atrophy (Leber's disease). Secondary neurodegeneration is caused primarily by necrosis. Non-limiting examples of conditions, which may result in secondary neurodegeneration, include destruction of neurons by neoplasm, edema, hemorrhage, stroke, trauma, immune attack, hypoxia, poisoning, metabolic defects, and infections.

The terms "extracellular DNA" and "cell-free DNA" are used interchangeably to refer to extracellular DNA (of eukaryotic or prokaryotic origin) found in blood, cerebrospinal fluid (CSF) or intestine of a patient.

As used herein, the terms "deoxyribonuclease" and "DNase" are used to refer to any enzyme that catalyzes the hydrolytic cleavage of phosphodiester linkages in the DNA backbone. A wide variety of deoxyribonucleases is known and can be used in the methods of the present invention. Non-limiting examples of useful DNases include, e.g., DNase I (e.g., human recombinant DNase I or bovine pancreatic DNase I), analogues of DNase I (such as, e.g., DNase X, DNase gamma, and DNAS1L2), DNase II, phosphodiesterase I, lactoferrin, and acetylcholinesterase. DNase I cleaves DNA preferentially at phosphodiester linkages adjacent to a pyrimidine nucleotide, yielding 5'5'-phosphate-terminated polynucleotides with a free hydroxyl group on position 3', on average producing tetranucleotides. DNase I acts on single-stranded DNA, double-stranded DNA, and chromatin.

The term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

In the context of the present invention insofar as it relates to neurodegeneration or any of the specific disease conditions recited herein, the terms "treat", "treatment", and the like mean to relieve or alleviate at least one symptom associated with such condition, or to slow or reverse the progression of such condition. Within the meaning of the present invention, the term "treat" also denotes to arrest, delay the onset (i.e., the period prior to clinical manifestation of a disease) and/or reduce the risk of developing or worsening a disease.

As used herein the term "therapeutically effective" applied to dose or amount refers to that quantity of a compound or pharmaceutical composition that is sufficient to result in a desired activity upon administration to a subject in need thereof. Within the context of the present invention, when the term "therapeutically effective" is used in connection with the use of deoxyribonuclease (DNase) to prevent, treat and/or inhibit progression of neurodegeneration or a specific disease associated with said neurodegeneration, it refers to an amount of DNase or a pharmaceutical composition containing DNase that is effective to relieve or alleviate at least one symptom associated with neurodegeneration or such disease, or to slow or reverse the progression of neurodegeneration or such disease. Note that when a combination of active ingredients is administered (e.g., a combination of DNase and another compound effective for preventing, treating and/or inhibiting progression of a disease associated with neurodegeneration) the effective amount of the combination may or may not include amounts of each ingredient that would have been effective if administered individually.

The phrase "pharmaceutically acceptable", as used in connection with compositions of the invention, refers to molecular entities and other ingredients of such compositions that are physiologically tolerable and do not typically produce untoward reactions when administered to a subject (e.g., a mammal such as a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

As used herein, the terms "subject" and "patient" refer to any mammal. In a preferred embodiment, the subject/patient is human.

As used in this specification and the appended claims, the singular forms "a," "an," and "the" include plural references unless the context clearly dictates otherwise.

In accordance with the present invention there may be employed conventional pharmacology and molecular biology techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M J. Gait ed. 1984); *Nucleic Acid Hybridization* (R D. Hames & S. J. Higgins eds. (1985)); *Transcription and Translation* (B. D. Hames & S. J. Higgins, eds. (1984)); *Animal Cell Culture* (R. I. Freshney, ed. (1986»; *Immobilized Cells and Enzymes* (IRL Press, (1986)); B. Perbal, *A Practical Guide To Molecular Cloning* (1984); F. M. Ausubel et al. (eds.), *Current Protocols in Molecular Biology*, John Wiley & Sons, Inc. (1994); among others.

Therapeutic Methods of the Invention

As demonstrated in the Examples section, below, both prokaryotic and eukaryotic extracellular DNA level in blood and cerebrospinal (CSF) fluid increases with worsening of neurological status in patients with senile dementia, Parkinson's and Alzheimer's' diseases. As further demonstrated herein, a large part of extracellular DNA in blood and CSF is intestinal bacterial DNA (e.g., derived from gastrointestinal microbiota). Hence, the monitoring of extracellular DNA from eukaryotic or prokaryotic origin can be useful for prognosis or monitoring progression of neurodegeneration. Monitoring may include, e.g., one or more of the following: determination of the amount of extracellular DNA, determination of the type of extracellular DNA (prokaryotic or eukaryotic, e.g., determined based on rRNA), determination of the presence and/or amount of specific DNA fragments (e.g., CpG motifs, CpG-like motifs, hyperconservative regions of 16S, rpoD, e.g., determined using RT-PCR or metagenomic analysis).

As further described herein, extracellular DNA from intestine, blood and CSF of patients suffering from neurodegenerative disorders can cross the blood brain barrier (BBB). This is unexpected, since BBB has been always considered as impermeable for large nucleic acid molecules (Evers M M. Antisense oligonucleotides in therapy for neurodegenerative disorders. Adv Drug Deliv Rev. 2015).

As further described herein, extracellular DNA from intestine, blood and CSF of patients suffering from neurodegeneration causes neuronal cell death and apoptosis. DNase treatment destroying such extracellular DNA significantly improves the nervous system function in these patients. The improvement assessment was performed according to widely accepted clinical diagnostic criteria of cognitive decline such as MMSE, PANSS, physical function, and/or functional tasks (see, e.g., Holmes et al., (1999) The British Journal of Psychiatry, 174(1), 45-50; Os et al., (2006) Acta Psychiatrica Scandinavica, 113(2), 91-95; O'Shea et al., (2002) Physical therapy, 82(9), 888-897; Rochester et al., (2004) 85(10), 1578-1585).

In one aspect, the invention provides a method for preventing, treating and/or inhibiting progression of neurodegeneration in a subject in need thereof, which method comprises administering to the subject a therapeutically effective amount of a DNase enzyme (e.g., DNase I, analogues of DNase I [such as, e.g., DNase X, DNase gamma, DNAS1L2], DNase II, phosphodiesterase I, lactoferrin, or acetylcholinesterase), wherein said amount of the DNase enzyme is effective to prevent or ameliorate at least one symptom of neurodegeneration.

DNase doses useful in the methods of the invention depend on the severity and course of the neurodegeneration, previous or concurrent therapy, the patient's clinical history and response to DNase, as well as the discretion of the attending physician. Preferably, such doses range from 0.5 to 20 mg/kg/day or 500 to 20000 Kunitz units (KU)/kg/day.

The administration of a DNase enzyme according to the methods of the invention can be performed by any suitable route. Specific non-limiting examples of useful routes of administration include intravenous, subcutaneous, intramuscular, delivery to cerebrospinal fluid (CSF), enteral (e.g., oral), rectal (e.g., by enema), and intranasal.

According to the methods of the invention, DNase can be administered either alone or in combination with other treatments useful for inhibiting progression or treatment of neurodegenerative diseases or other encompassed nervous system dysfunctions (e.g., bipolar disorder, migraine, schizophrenia, epilepsy). Non-limiting examples of such additional treatments include, e.g., histone acetyltransferase activators, cyclin-dependent protein kinase 5 inhibitors, neurotrophin mimetics, semaphorin-4D blockers, microsomal prostaglandin E synthase-1 inhibitors, levodopa, and N-methyl-d-aspartate (NMDA) receptor inhibitors (e.g., memantine).

Pharmaceutical Compositions of the Invention

In certain embodiments, a DNase enzyme can be formulated in a pharmaceutical composition with a pharmaceutically acceptable carrier or excipient.

The formulations used in the methods of the invention may conveniently be presented in unit dosage form and may be prepared by methods known in the art. The amount of active ingredients that can be combined with a carrier material to produce a single dosage form will vary depending upon the subject being treated and the particular mode of administration. The amount of active ingredients that can be combined with a carrier material to produce a single dosage form will generally be that amount of the compound which produces a therapeutic effect.

In general, the formulations can be prepared with a liquid carrier, or a finely divided solid carrier, or both, and then, if necessary, shaping the product.

Pharmaceutical compositions suitable for parenteral administration may comprise DNase in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

Injectable depot forms can be made by forming microencapsule matrices of one or more active ingredients in biodegradable polymers such as polylactide-polyglycolide. Depending on the ratio of active ingredient to polymer, and the nature of the particular polymer employed, the rate of active ingredient's release can be controlled. Examples of other biodegradable polymers include poly(orthoesters) and poly(anhydrides). Depot injectable formulations are also prepared by entrapping the active ingredients in liposomes or microemulsions which are compatible with body tissue.

Formulations for oral administration can be in the form of capsules, cachets, pills, tablets, powders, granules, or as a solution or a suspension in an aqueous or non-aqueous liquid (e.g., as a mouthwash, as a composition to be swallowed, or as an enema), or as an oil-in-water or water-in-oil liquid emulsion, and the like, each containing a predetermined amount of one or more active ingredients.

In solid dosage forms for oral administration (capsules, tablets, pills, dragees, powders, granules, and the like), one or more active ingredients (e.g., DNase and optionally another compound for treatment of a neurodegenerative disease) can be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8)

absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Suspensions, in addition to one or more active ingredients, can contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

The DNase compositions of the invention may further comprise agents, which facilitate DNase delivery across the blood brain barrier (BBB). Non-limiting examples of such useful agents include, e.g., an implantable reservoir (Omaya reservoir), polysialation of DNase, functionalized nanocarriers (e.g., nanoparticles coated with transferrin or transferrin receptor [TR] antibodies), exosomes, liposomes (e.g., liposomes coated with targeting molecules such as antibodies, Trojan Horses Liposomes [THL]), antibodies (e.g., antibodies against transferrin receptor [TR] or insulin receptor [HIR], BBB transmigrating Llama single domain antibodies (sdAb)), chimeric peptides (e.g., Angiopeps derived from proteins expressing the Kunitz domain), low-density lipoprotein receptor related proteins 1 and 2 (LRP-1 and 2), diphtheria toxin receptor (DTR), mesenchyme stem cells, receptor-associated protein, apolipoprotein E, melanotransferrin/p97, etc.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1. Extracellular Circulating DNA from Blood and CSF Promotes Neuronal Cell Death For neuronal cultures, cerebral cortices were removed from embryonic day (E) 15-17 Sprague Dawley rat embryos. Cortical explants were dissected into pieces of about 200-400 μm$^2$ using fine needles and dissociated with the Papain Dissociation System (Worthington Biochemicals) according to the manufacturer's instructions and further kept on ice-cold minimum essential medium (Gibco). Neurons were plated on 13 mm diameter glass coverslips coated first with poly-D-lysine (10 μg/ml in PBS) followed by laminin (10 μg/ml in PBS) (Gibco) and cultured at 37° C. in a humidified 8% CO$_2$ (v/v) atmosphere for 24-48 hrs in Neurobasal medium with 1% (v/v) Antibiotic-Antimycotic (Gibco).

Extracellular DNA was extracted from plasma and CSF of a patient with a severe stage of Alzheimer's disease using QIAamp Circulating Nucleic Acid Kit according to manufacturers' instructions. In order to assess biological effect of such extracellular DNA on neurons, samples of extracellular DNA were added to cortical neuronal cultures. Neuronal cell death was determined in dissociated cortical neurons cultured for 48 hours. After initial period, extracellular DNA samples (100 and 200 mkg/ml dose levels) were applied for a further 24 hours. Neuronal cell death was assessed by CytoTox-Glo™ Cytotoxicity Assay (Promega). Luminescence proportional to the number of dead cells was measured using a Promega GloMax 96 luminometer and was expressed in relative luminescence units (RLU).

Induction of apoptosis marker caspase 3 was determined in dissociated cortical neurons cultured for 48 hours. After initial period, extracellular DNA samples (100 and 200 mkg/ml dose levels) were applied for a further 24 hours. Cells were than fixed in 4% (w/v) paraformaldehyde (PFA) and incubated for 1 hour with cleaved caspase 3 antibody (Abcam) diluted 1:500 in PBS. Cells were washed and incubated for 1 hour with goat anti-rabbit polyclonal Alexa Fluor 488 antibodies for caspase 3 (Invitrogen) in PBS prior to washing and counting.

TABLE 1

|  | Extracellular DNA 0 | | Extracellular DNA 100 mkg/ml | | Extracellular DNA 200 mkg/ml | |
| --- | --- | --- | --- | --- | --- | --- |
|  | RLU | % Caspase positive | RLU | % Caspase positive | RLU | % Caspase positive |
| Extracellular DNA (blood) | 1 100 | 3% | 4 650 | 10% | 12 700 | 32% |
| Extracellular DNA (CSF) | 700 | 6% | 6 250 | 15% | 9 100 | 25% |
| Extracellular DNA (blood) + DNASE I* (5 mkg/ml) | 900 | 2% | 2 300 | 5% | 3 200 | 9% |
| Extracellular DNA (CSF) + DNASE I* (5 mkg/ml) | 1050 | 3% | 1 700 | 8% | 4 500 | 7% |

*DNase I used was human recombinant DNASE 1 manufactured by Catalent (Madison, USA).

From the data in Table 1, it follows that extracellular DNA from both blood and CSF induces cytotoxicity and upregulation of apoptosis marker caspase 3 in cultured neurons in a dose dependent manner. DNase I protects neurons from toxicity induced by extracellular DNA.

Example 2. Evaluation of Bacterial Extracellular DNA in Blood and CSF of a Patient with Alzheimer's Disease Extracellular DNA was extracted from plasma and CSF of a patient with a severe stage of Alzheimer's disease and a healthy volunteer (age- and sex-matched) using QIAamp Circulating Nucleic Acid Kit according to manufacturers' instructions. Quantification of bacterial extracellular DNA was done using CFX96 Touch™ Real-Time PCR Detection System. We have used universal bacterial DNA PCR primers 1369F and 1492R (Bacterial 16S rRNA).

| 1369F (SEQ ID NO: 1) | CGGTGAATACGTTCYCGG |
| --- | --- |
| 1492R (SEQ ID NO: 2) | GGWTACCTTGTTACGACTT |

The threshold cycles are presented in the table below:

TABLE 2

| Group | Sample | Cq |
|---|---|---|
| Alzheimer's disease | Serum | 16.45 |
| | CSF | 18.10 |
| Healthy volunteers | Serum | 31.12 |
| | CSF | 29.09 |

As follows from the data in Table 2, serum and CSF of a patient with a severe stage of Alzheimer's disease contains significantly more bacterial DNA as compared to a healthy volunteer.

Example 3. Extracellular Circulating DNA from Blood Penetrates the Blood Brain Barrier Extracellular DNA was extracted from plasma of a patient diagnosed with senile dementia using QIAamp Circulating Nucleic Acid Kit. Iodination of extracellular DNA was performed using Iodo-Gen reagent as described (Piatyszek A., et al., Analytical Biochemistry, 1988, V172, pp. 356-359). Specific activity of labeled extracellular DNA was approximately 30 mkCi/mkg. The preparation of labeled extracellular DNA in 1 ml of PBS solution (approx. 3.0 mkCi, 100 ng) was slowly infused (0.1 ml/mn) into carotid artery of an anesthetized female Sprague Dawley rat. In one hour, the rat was euthanized with chloroform, the brain was removed and fixed in formalin solution. Paraffin sections were stained with Ilford L4 emulsion. Accumulation of the labeled extracellular DNA in brain was studied using standard visual histoautoradiographic technique (FIG. 1). Accumulation of injected extracellular DNA in rat brain parenchyma indicates that it penetrates blood brain barrier (BBB).

Example 4. Use of DNase for Treatment of Senile Dementia

Patient K., age 72, male has was diagnosed with senile dementia 4 years ago with gradual development of bradykinesia, deterioration of short-term memory and attention. Gradually the following symptoms progressed: aspontaneity, lack of initiative, emotional lability, drowsiness. For 3 years the patient has been taking levodopa. A moderate positive effect was observed. However, during the last 18 prior symptoms became more pronounced, also hypokinesia and postural disorders began to manifest.

The patient was administered bovine pancreatic DNase I (Samson Med, Russia) in the amount of 2500 Kunitz units/kg three times per day orally in capsules. The effectiveness of the DNase treatment was assessed using the mini-mental state examination scale (MMSE) after 14 and 30 days. The results of the study are shown in Table 3.

TABLE 3

| MMSE score points | | |
|---|---|---|
| D 0 | D 14 | D 30 |
| 16 | 19 | 23 |

Human blood plasma DNA from the patient was quantified using real-time PCR (RT-PCR) assay for three different markers sequences: ALU (J1), c-MYC and b-GLOB (ALU primer was GTCAGGAGATCGAGACCATCCC (SEQ ID NO: 3), c-MYC primer was AAACACAAACTT-GAACAGCTAC (SEQ ID NO: 4), b-GLOB primer was GGTTGGCCAATCTACTCCCAGG (SEQ ID NO: 5) two month prior to the DNase treatment and immediately before the start of the DNase treatment. The threshold cycles are presented in the table below.

TABLE 4

| | Total cf DNA | | |
|---|---|---|---|
| | Alu | C-myc | β-Glob |
| −60 days | 14.47 ± 0.109 | 28.62 ± 0.294 | 29.49 ± 0.161 |
| Prior treatment starts | 14.6 ± 0.012 | 29.42 ± 0.021 | 31.86 ± 0.817 |

Figure 2:
FIG. 2 shows electrophoregrams of blood extracellular DNA of a patient before administration of DNase (left column) and one month after the start of DNase treatment (right column).

Electrophoregrams (agarose gels) of blood extracellular DNA of the patient before the DNase treatment (left column) and one month after the start of the treatment (right column) are presented in FIG. 2.

As demonstrated above, the progression of clinical symptoms in a patient with senile dementia is accompanied by elevation of the level of circulating extracellular DNA in blood. DNase treatment destroying blood extracellular DNA has a positive clinical effect on dementia symptoms.

Example 5. Relief of Exacerbation of Bipolar Disorder Using DNase

Patient: M., age 63, male. Diagnosis: primary illness—exacerbation of bipolar disorder, manic episode. At the beginning of the treatment, complained about being irritable, having a desire to scream away, nightmares. Examination revealed that the patient was highly active, would leave the room all of a sudden, manifested disinhibition (constantly asked questions, would often start to sing) and irritability (was easily irritated by repetitive questions).

Before the beginning of the DNase treatment, the total score of assessment using Excited Component of the Positive and Negative Syndrome Scale (PANSS-EC) amounted to 29. Patient received a one-time intravenous injection of human recombinant DNase I (Catalent, Madison, USA) in the amount of 50 Kunitz units/kg for 3 hours. After DNase treatment, a significant alleviation of the symptoms was observed, total score of PANSS-EC amounted to 8, no psychomotor excitement could be observed.

Therefore, the administration of DNase has a positive effect when treating exacerbation of bipolar disorder.

Example 6. Use of DNase for Treatment of Schizophrenia

Patient: L. age 38, female. Diagnosis: schizophrenia, paranoid type, paroxysmal course of the disease, paranoid-hallucinatory syndrome. Before the DNase treatment, the patient complained about hearing voices "inside her head", she also believed that her colleagues were trying to poison her. The patient was sitting in the unnatural posture, also a pronounced tremor of the upper extremities was observed, the tremor would subside upon movement. Emotional disorders were discovered, as well as thought disorders (slow thinking, derailment, illogicality). The total score of assessment using the Positive and Negative Syndrome Scale (PANSS) amounted to 24 and 22, respectively.

The patient began taking bovine pancreatic DNase I (Samson Med, Russia) orally in capsules in the amount of 3000 Kunitz units (KU)/kg three times per day. The results of the study are shown in Table 5.

TABLE 5

| Group | Scores according to the Positive and Negative Syndrome Scale (PANSS) | |
| --- | --- | --- |
| | Positive Syndrome Scale, total score ± statistical deviation | Negative Syndrome Scale, total score ± statistical deviation |
| Before the treatment | 24 | 22 |
| On day 2 of the treatment | 13 | 18 |
| On day 5 of the treatment | 11 | 13 |

Therefore, the administration of DNase has a positive effect when treating schizophrenia.

Example 7. Use of DNase for Treatment of Alzheimer Disease

Patient G., age 77, male. The patient was diagnosed with Alzheimer's disease based on clinical data and indicative MRI changes. Starting from month 14 after being diagnosed, the patient started taking Memantine. However, the clinical symptoms continued to deteriorate: memory impairments progressed, impairments of speech and coordination began to manifest, as well as disorientation. By month 20 after being diagnosed the patient had all of the above-mentioned symptoms progressing and stopped going around on his own. By the time the DNase administration began, the patient was in stupor, also urinary and fecal incontinence were observed.

Bovine pancreatic DNase I (Samson Med, Russia) was administered orally in capsules in the amount of 4000 Kunitz units/kg three times per 24 hours. The effectiveness was assessed using the MMSE mini-scale, 5 and 30 days after the beginning of the DNase treatment. The results of the study are shown in Table 6.

TABLE 6

| Day of beginning of the treatment | Treatment | MMSE score (points) |
| --- | --- | --- |
| Before the DNase treatment | Memantine | 3 |
| 5 | DNase | 15 |
| 30 | DNase | 19 |

The human blood plasma DNA from the patient was quantified using conventional real time PCR (RT-PCR) assay for three different markers sequences: ALU (J1), c-MYC and b-GLOB (ALU primer was GTCAG-GAGATCGAGACCATCCC (SEQ ID NO: 3), c-MYC primer was AAACACAAACTTGAACAGCTAC (SEQ ID NO: 4), b-GLOB primer was GGTTGGCCAATC-TACTCCCAGG (SEQ ID NO: 5) in total fraction of patient's extracellular DNA one month prior to the DNase treatment, immediately before the treatment start, and 30 days after initiation of the DNase treatment. The results are presented at Table 7.

TABLE 7

| | Total cf DNA | | |
| --- | --- | --- | --- |
| | Alu | C-myc | β-glob |
| 30 Days before the DNase treatment | 10.52 ± 0.095 | 27.32 ± 0.239 | 29.07 ± 0.326 |
| Immediately before the DNase treatment | 11.72 ± 0.056 | 27.86 ± 0.161 | 30.2 ± 0.345 |
| 30 days after the DNase treatment | 10.48 ± 0.027 | 26.78 ± 0.129 | 29.2 ± 0.379 |

As early as on day 5 after the beginning of the DNase treatment, a significant improvement of the cognitive functions was observed. Speech and thinking went back to normal, the patient was able to get up, get dressed and go around unaided.

Therefore, the administration of DNase has a positive effect on treatment of Alzheimer's disease. The positive clinical effect of DNase treatment develops alongside with reduction of the level of circulating extracellular DNA in the blood.

Figure 3A:
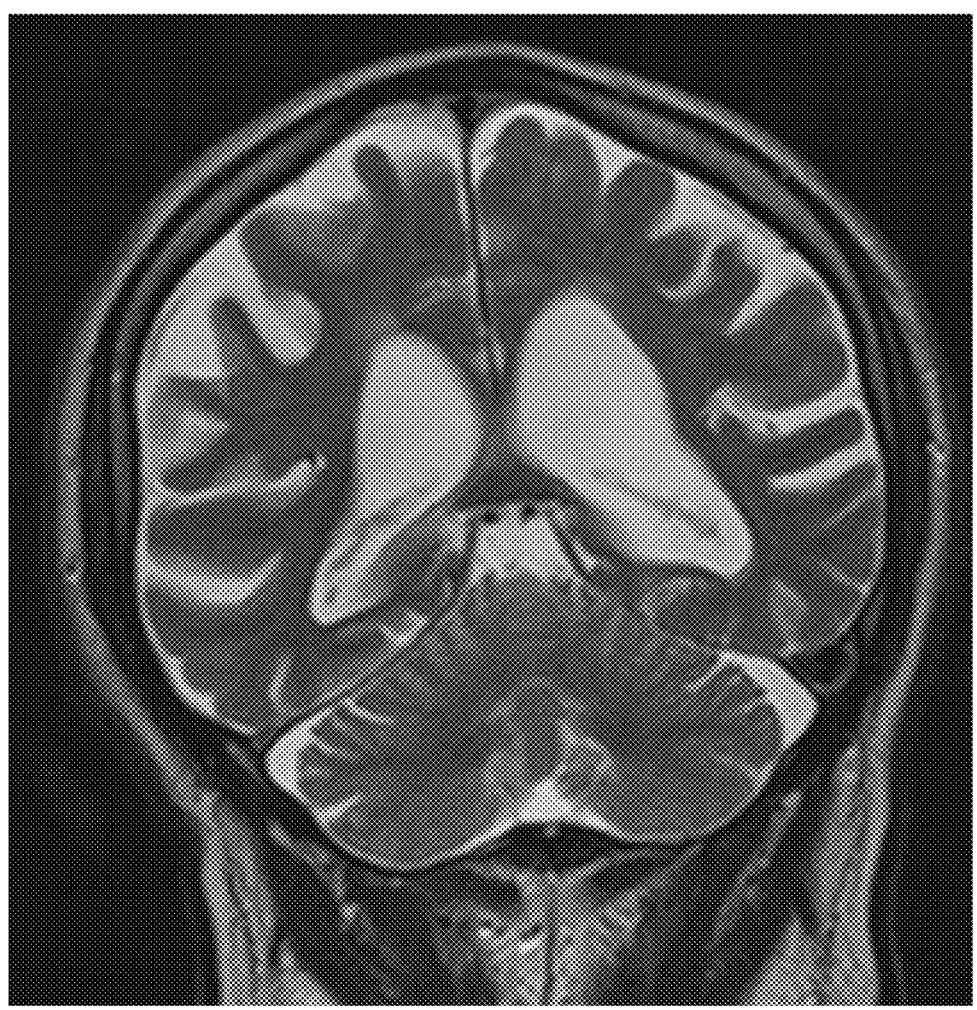
FIGS. 3A-B are T1 MRI images showing atrophy and extensive gliosis of the left frontoparietal region in the brain of a patient with severe Alzheimer's disease. Images (A) and (B) depict volume loss in end-stage Alzheimer's disease with mild changes to the periventricular white matter. (A) Coronal T1 MRI of showing marked progressive cortical atrophy of the parietal regions. (B) Transverse T1 MRI showing bilateral marked atrophy.
Figure 3B:
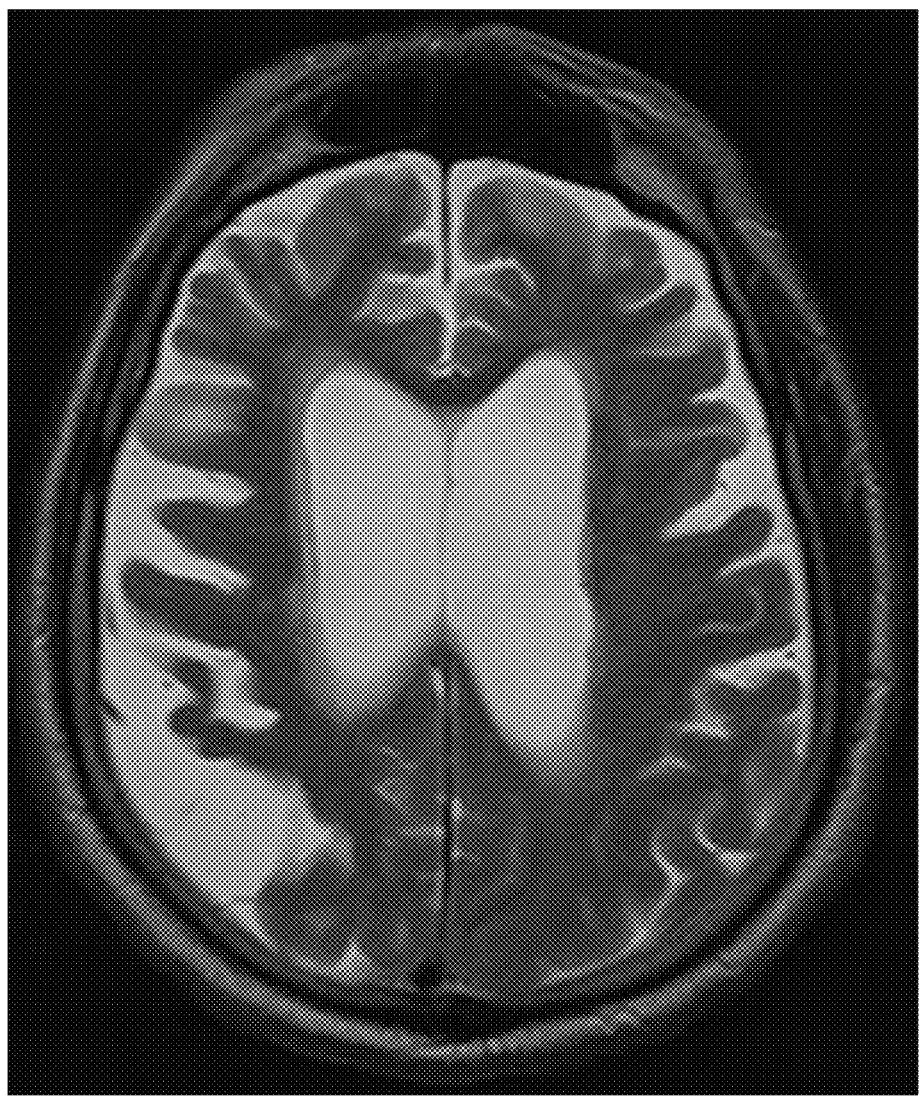

Example 8. Use of DNase for Treatment of Lewy Body Variant of Alzheimer's Disease A 77-year-old Caucasian male was diagnosed with dementia secondary to late-onset Alzheimer's disease 30 months prior to his presentation at clinic, exhibiting behavioral disturbances, cognitive decline, and decreased ability to engage in activities of daily living. Approximately 14 months following the initial diagnosis, the patient began treatment with 10 mg of memantine per day (Reisberg et al., N Engl J Med. 2003; 348:1333-1341; Danysz et al., Br J Pharmacol. 2012; 167:324-352), though his cognitive condition continued to deteriorate, rapidly progressing to include such behavioral changes as aggressiveness and disinhibition, in addition to progressive amnesic syndrome, aphasia, bradykinesia, shuffling gait, loss of balance, and urinary incontinence. Further, the patient experienced a 20-pound weight loss, which is ordinarily indicative of a poor prognosis in patients suffering from Alzheimer's disease (Soto et al., Journal of Alzheimer's Disease (2012) 28:647-654; Soto et al., J Am Geriatr Soc. 2015; 63:651-658; White et al., J Am Geriatr Soc.1998; 46:1223-1227). Analysis of cranial MRIs revealed age-appropriate losses in volume and mild changes to the periventricular white matter (FIGS. 3A-B).

Thirteen months following initiation of memantine treatment, the patient's total scores on the Mini-Mental State Examination (MMSE) and Functional Assessment Staging Test (FAST) were 10 and 5 points, respectively. He lost points on orientation to time and place, attention, memory, and visuospatial construction, and the patient was noticeably slower in completing the tasks. The patient experienced additional difficulty in navigating turns and corners when walking, resulting in recurrent falls, and exhibited fluctuating levels of consciousness, alternating between periods of frank confusion and lucidity. However, he experienced no visual or auditory hallucinations.

A further three months later, and a total of 16 months following initiation of memantine treatment, the patient experienced further deterioration of cognitive function. The patient had fluctuating level of consciousness. His cognition fluctuated between periods of frank confusion and lucidity, however he had no visual or auditory hallucinations. He was unable to remember his name, the calendar date, day of the week, year, or place and could not recognize family members. Additional impairments included slurred speech, expressive aphasia, loss of bowel/bladder control, and lack of coordination marked by an inability to sit, stand, or walk unassisted. The patient became unresponsive to stimuli, with an MMSE score of 3 and a FAST score of 7.

One month later, the patient's relatives provided informed consent for treatment with 40 mg of human recombinant DNase I (1500 KU/mg; Samson Med, Russia) given orally 3 times a day in conjunction with his continued memantine therapy (10 mg daily). The DNase I was well tolerated, and no adverse or unanticipated events were registered.

The patient demonstrated considerable cognitive improvement beginning on the second day of DNase I treatment, becoming partially oriented to time and place, and once again recognizing and remember the names of family members. He further became able to dress himself, including tying shoelaces and buttons, as well as walk independently, feed himself, and use an exercise bike. Neurologic abnormalities affecting gait were significantly reduced. His MMSE score increased dramatically from 3 to 16, and his FAST score was reduced from 7 to 5. However, he continued to score low on the MMSE for measures of orientation to time and place, memory, and visuospatial construction.

Two months following the initiation of DNase I treatment (19 months following initiation of memantine treatment), the patient exhibited an MMSE score of 18 and a FAST score of 4. Moderate improvements in memory were observed, although visuospatial construction continued to decline. He was better able to speak and interact with others, recognize relatives, and actively attend to television programs. The patient further became able to perform calculations, play piano, chess, and walk independently.

The above data demonstrate that the administration of DNase has a positive effect on treatment of Alzheimer's disease. Treatment with DNase I in the present case allowed the patient to withdraw form a terminal state and resulted in significant improvements in cognitive and behavioral function, including the ability to walk and perform everyday tasks with near independence. Significant recovery was observed in all areas of cognitive and motor function, indicating the possibility of a DNase-sensitive target involved in generating the symptoms of Alzheimer's disease. Cell-free DNA, including bacteria-derived DNA, may be one such target (Holdenrieder et al., Clin Chem. 2005; 51:1544-1546).

Example 9. Use of DNase for Treatment of Parkinson's Disease

Patient S., age 58, female, has been suffering from Parkinson's disease for 7 years. For the last 5 years she has been treated with levodopa. One month before the study, there was a significant deterioration in patient's condition, namely: significant increase of tremor of the right hand, appearance of involuntary movements of hands in the form of generalized choreoathetosis, rigidity of extremities, difficulties with getting up from the bed in the morning, frequent nocturnal urination (6-7 times).

The patient began taking bovine pancreatic DNase I (Samson Med, Russia) orally in capsules in the amount of 1500 Kunitz units/kg three times per day. Assessment was done using unified Parkinson's disease rating scale (UPDRS), observation was performed during 6 months.

Human blood plasma DNA from the patient was quantified using conventional real time PCR (RT-PCR) assay for ALU sequence (TPALU1: GTAAGAGTTCCGTAACA-GGACAGCT (SEQ ID NO: 6)) in total fraction of patient's extracellular DNA one month prior to the DNase treatment, immediately before the treatment, and 3 months after the initiation of the treatment. The threshold cycles are presented in Table 8.

TABLE 8

| Observation time, months | Cf DNA quantity (ALU) | UPDRS (points) |
| --- | --- | --- |
| 0 | 9.56 ± 0.047 | 22 |
| 1 | 9.43 ± 0.012 | 17 |
| 3 | 8.93 ± 0.042 | 16 |
| 12 | — | 14 |
| 24 | — | 12 |

By month 6 of taking DNase I, a significant improvement of the patient's condition was observed: morning akinesia, rigidity of movements and tremor of hands decreased; the number of nocturnal urinations dropped to one time per night.

It follows, that DNase administration has a positive effect on treatment of Parkinson's disease. This positive effect develops alongside with reduction of the level of circulating extracellular DNA in the blood.

Example 10. Use of DNase for Treatment of Amyotrophic Lateral Sclerosis

The studies were performed on mice with knockout of SOD1 enzyme, with hyperexpression of G93A-hSOD1 protein, which is a generally accepted model of amyotrophic lateral sclerosis (ALS) (Gurney, New England Journal of Medicine (1994) 331: 1721-1722). Two groups of animals were formed, each consisting of 10 animals (Jackson Laboratory, Bar Harbor, Me.). The animals were housed in a room with 12 hour light cycle and provided with free access to water and food. Polysialated DNAse was prepared as described in PCT/GB2007/002839. Briefly: 20 molar excess of oxidized 26 kDa polysialic acid (PSA) was dissolved in buffer and the pH adjusted to 6.0. Human recombinant DNase I DNAse (Catalent) and 50 mM (final concentration) sodium cyanoborohydride were then added, the pH re-adjusted, and reaction mixture brought to the required volume. Reactions were carried out at 37±1° C. with gentle shaking for 18 hours. DNAse-PSA conjugates were purified using hydrophobic interaction chromatography (HIC)-Phenyl-sepharose matrix, starting buffer containing 2.0 M ammonium sulphate, elution in buffer without ammonium sulphate. Elution fractions are then applied to ion exchange matrix Q-sepharose Fast Flow, and eluted with buffer containing sodium chloride. Purification of conjugates was confirmed by size-exclusion-high performance liquid chromatography (SE-HPLC).

Mice from Group 1 received no treatment (the control group); mice from Group 2 received human polysialated recombinant DNase I dosed at 50 mg/kg subcutaneously once a day. Survival time of the animals was used as an assessment criterion. Results are shown in Table 9.

TABLE 9

| | Percentage of surviving animals within the group (%) | |
| --- | --- | --- |
| Day of the study | Group 1 | Group 2 |
| 60 | 70 | 100 |
| 90 | 50 | 100 |
| 120 | 20 | 100 |
| 150 | 0 | 70 |
| 180 | 0 | 60 |

TABLE 9-continued

Percentage of surviving animals within the group (%)

| Day of the study | Group 1 | Group 2 |
|---|---|---|
| 210 | 0 | 50 |
| 240 | 0 | 20 |

It follows that administration of DNase I has a positive effect on survival of mice suffering from ALS.

Example 11. Use of DNase for Treatment of Systemic CNS Atrophy

Huntington's disease was chosen as an example of systemic atrophies of the central nervous system. Studies were performed on R6/2 transgenic mice expressing exon 1 of the gene that encodes glutamine, which is a generally accepted model of Huntington's disease (Miller et al., Neuroscience (2008) 153: 329-337). Three groups of animals were formed, each consisting of 10 animals (Charles River Laboratories). The animals were housed in a room with 12 hour light cycle and provided with free access to water and food. Mice from Group 1 received no treatment; mice from Group 2 received human recombinant DNase I (Catalent, Madison, USA) in the amount of 25000 mg/kg (2 times per 24 hours, intramuscularly); mice from Group 3 received DNase in the amount of 25 mg/kg (once a week, into CSF, using ICV bolus injection technique). Survival time of the animals was used as an assessment criterion. Results are shown in Table 10.

TABLE 10

| | Survival in groups (%) | | |
|---|---|---|---|
| Week | Group 1 | Group 2 | Group 3 |
| 6 | 100 | 100 | 100 |
| 9 | 70 | 100 | 100 |
| 12 | 10 | 100 | 100 |
| 15 | 0 | 100 | 100 |
| 18 | 0 | 100 | 90 |
| 21 | 0 | 70 | 60 |
| 24 | 0 | 50 | 40 |

Therefore, the administration of DNase I has a positive effect on treatment of Huntington's disease.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

The invention claimed is:

1. A method for treating and/or inhibiting progression of primary neurodegeneration in a patient in need thereof, comprising administering to said patient a therapeutically effective amount of a DNase enzyme, wherein the neurodegeneration is associated with an increased level of extracellular DNA of prokaryotic origin in blood or cerebrospinal fluid or intestine of said patient, and wherein said therapeutically effective amount of the DNase enzyme is sufficient to decrease the average molecular weight of said extracellular DNA of prokaryotic origin.

2. The method of claim 1, wherein the increased level of extracellular DNA of prokaryotic origin in blood or cerebrospinal fluid or intestine of said patient is higher than a control level of extracellular DNA of prokaryotic origin in blood or cerebrospinal fluid or intestine.

3. The method of claim 2, wherein the control level is the level of extracellular DNA of prokaryotic origin in blood or cerebrospinal fluid or intestine of a healthy age-matched individual or an average level of extracellular DNA of prokaryotic origin in blood or cerebrospinal fluid or intestine of several healthy age-matched individuals.

4. The method of claim 1, wherein said therapeutically effective amount of the DNase enzyme is sufficient to decrease the average molecular weight of said extracellular DNA of prokaryotic origin in blood or cerebrospinal fluid or intestine of the patient.

5. The method of claim 1, wherein said therapeutically effective amount of the DNase enzyme is sufficient to decrease the average molecular weight of said extracellular DNA of prokaryotic origin as measured by gel electrophoresis.

6. The method of claim 1, wherein said DNase is a recombinant DNase.

7. The method of claim 1, wherein said DNase is DNase I.

8. The method of claim 1, wherein said DNase has an extended half-life, wherein said DNase is conjugated with polysialic acid or protected from binding to actin by modification of its actin binding site, thereby extending the half-life of said DNase.

9. The method of claim 1, wherein said DNase is administered by intravenous, subcutaneous or intramuscular route.

10. The method of claim 9, wherein said DNase is DNase I and is administered in the amount of at least 0.04 mg per kg per day during at least one day.

11. The method of claim 9, wherein said DNase is DNase I and is administered in the amount of 0.05-10000 Kunitz units per kg per day during at least one day.

12. The method of claim 1, wherein said DNase is administered enterally.

13. The method of claim 12, wherein said DNase is administered orally.

14. The method of claim 12, wherein said DNase is DNase I and is administered in the amount of at least 0.04 mg per kg per day during at least one day.

15. The method of claim 12, wherein said DNase is DNase I and is administered in the amount of 0.05-10000 Kunitz units per kg per day during at least one day.

16. The method of claim 1, wherein said DNase is administered into cerebrospinal fluid.

17. The method of claim 16, wherein said DNase is DNase I and is administered in the amount of at least 0.1 mg per day.

18. The method of claim 1, wherein said patient has been diagnosed with Alzheimer's disease.

19. The method of claim 18, wherein said Alzheimer's disease is a late-onset Alzheimer's disease.

20. The method of claim 1, wherein said patient has been diagnosed with Parkinson's disease.

21. The method of claim 1, wherein said patient has been diagnosed with Amyotrophic Lateral Sclerosis.

22. The method of claim 1, wherein said patient has been diagnosed with Huntington's disease.

23. The method of claim 1, wherein said patient has been diagnosed with schizophrenia.

24. The method of claim 1, wherein said patient has been diagnosed with bipolar disorder.

25. The method of claim 1, wherein the patient is human.

26. The method of claim 1, wherein said DNase is administered for at least 1 month.

27. The method of claim 26, wherein said DNase is administered for at least 6 months.

28. The method of claim 1, wherein said therapeutically effective amount of the DNase enzyme is sufficient to decrease the neurotoxicity of said extracellular DNA.

29. The method of claim 1, wherein the administration of the DNase enzyme results in an improvement of a nervous system function in said patient.

30. The method of claim 1, further comprising assessing an improvement of a nervous system function in said patient.

\* \* \* \* \*

SEQUENCE LISTING

```
<160> NUMBER OF SEQ ID NOS: 6

<210> SEQ ID NO 1
<211> LENGTH: 18
<212> TYPE: DNA
<213> ORGANISM: Artificial sequence
<220> FEATURE:
<223> OTHER INFORMATION: Primer 1369F

<400> SEQUENCE: 1
cggtgaatac gttcycgg                                                    18

<210> SEQ ID NO 2
<211> LENGTH: 19
<212> TYPE: DNA
<213> ORGANISM: Artificial sequence
<220> FEATURE:
<223> OTHER INFORMATION: Primer 1492R

<400> SEQUENCE: 2
ggwtaccttg ttacgactt                                                   19

<210> SEQ ID NO 3
<211> LENGTH: 22
<212> TYPE: DNA
<213> ORGANISM: Artificial sequence
<220> FEATURE:
<223> OTHER INFORMATION: ALU Primer

<400> SEQUENCE: 3
gtcaggagat cgagaccatc cc                                               22

<210> SEQ ID NO 4
<211> LENGTH: 22
<212> TYPE: DNA
<213> ORGANISM: Artificial sequence
```

```
<220> FEATURE:
<223> OTHER INFORMATION: c-MYC Primer

<400> SEQUENCE: 4
aaacacaaac ttgaacagct ac                                              22

<210> SEQ ID NO 5
<211> LENGTH: 22
<212> TYPE: DNA
<213> ORGANISM: Artificial sequence
<220> FEATURE:
<223> OTHER INFORMATION: b-GLOB Primer

<400> SEQUENCE: 5
ggttggccaa tctactccca gg                                              22

<210> SEQ ID NO 6
<211> LENGTH: 25
<212> TYPE: DNA
<213> ORGANISM: Artificial sequence
<220> FEATURE:
<223> OTHER INFORMATION: TPALU1 Primer

<400> SEQUENCE: 6
gtaagagttc cgtaacagga cagct                                           25
```